(12) United States Patent
Worrell et al.

(10) Patent No.: US 9,237,923 B2
(45) Date of Patent: Jan. 19, 2016

(54) SURGICAL INSTRUMENT WITH PARTIAL TRIGGER LOCKOUT

(71) Applicant: Ethicon Endo-Surgery, Inc., Cincinnati, OH (US)

(72) Inventors: Barry C. Worrell, Centerville, OH (US); Jonathan T. Batross, Mason, OH (US); Michael J. Stokes, Cincinnati, OH (US); David A. Witt, Maineville, OH (US); Chad P. Boudreaux, Cincinnati, OH (US); David K. Norvell, Monroe, OH (US); Matthew C. Miller, Cincinnati, OH (US); Timothy G. Dietz, Wayne, PA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 132 days.

(21) Appl. No.: 13/832,754

(22) Filed: Mar. 15, 2013

(65) Prior Publication Data

US 2014/0276736 A1 Sep. 18, 2014

(51) Int. Cl.
*A61B 18/14* (2006.01)
*A61B 18/00* (2006.01)

(52) U.S. Cl.
CPC ...... *A61B 18/1445* (2013.01); *A61B 2018/0063* (2013.01); *A61B 2018/00345* (2013.01); *A61B 2018/00589* (2013.01); *A61B 2018/00601* (2013.01); *A61B 2018/00607* (2013.01); *A61B 2018/1455* (2013.01)

(58) Field of Classification Search
USPC ..................................... 606/48, 51
See application file for complete search history.

(56) References Cited

U.S. PATENT DOCUMENTS

| 4,805,823 | A | 2/1989 | Rothfuss |
|---|---|---|---|
| 5,415,334 | A | 5/1995 | Williamson, IV et al. |
| 5,465,895 | A | 11/1995 | Knodel et al. |
| 5,597,107 | A | 1/1997 | Knodel et al. |
| 5,632,432 | A | 5/1997 | Schulze et al. |
| 5,673,840 | A | 10/1997 | Schulze et al. |
| 5,704,534 | A | 1/1998 | Huitema et al. |
| 5,814,055 | A | 9/1998 | Knodel et al. |
| 6,500,176 | B1 | 12/2002 | Truckai et al. |
| 6,783,524 | B2 | 8/2004 | Anderson et al. |

(Continued)

FOREIGN PATENT DOCUMENTS

WO  WO 2011/044343  4/2011

OTHER PUBLICATIONS

U.S. Appl. No. 61/410,603, filed Nov. 5, 2010.

(Continued)

*Primary Examiner* — Nicole F Lavert
(74) *Attorney, Agent, or Firm* — Frost Brown Todd LLC

(57) ABSTRACT

An end effector comprises a first jaw, a second jaw, a firing beam, and a lockout feature. The second jaw pivots relative to the first jaw from an open position to a closed position. The firing beam has a sharp distal end and translates between the first and second jaws. The firing beam translates from a proximal position to a first distal position to pivot the second jaw to the closed position. The end effector applies bipolar RF energy when the firing beam is in the first distal position. The firing beam then translates to a second distal position to sever tissue captured between the first and second jaws. The lockout feature prevents the firing beam from advancing from the first distal position to the second distal position until the lockout feature is actuated.

20 Claims, 37 Drawing Sheets

(56) References Cited

U.S. PATENT DOCUMENTS

| | | |
|---|---|---|
| 6,978,921 B2 | 12/2005 | Shelton, IV et al. |
| 7,000,818 B2 | 2/2006 | Shelton, IV et al. |
| 7,112,201 B2 | 9/2006 | Truckai et al. |
| 7,125,409 B2 | 10/2006 | Truckai et al. |
| 7,143,923 B2 | 12/2006 | Shelton, IV et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,303,108 B2 | 12/2007 | Shelton, IV et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,434,715 B2 | 10/2008 | Shelton, IV et al. |
| 7,721,930 B2 | 5/2010 | McKenna et al. |
| 8,408,439 B2 | 4/2013 | Huang et al. |
| 8,453,914 B2 | 6/2013 | Laurent et al. |
| 8,461,744 B2 | 6/2013 | Wiener et al. |
| 8,795,327 B2 | 8/2014 | Dietz et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0077131 A1* | 3/2008 | Yates et al. ............ 606/48 |
| 2008/0200940 A1 | 8/2008 | Eichmann et al. |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 | 4/2011 | Boudreaux et al. |
| 2012/0022526 A1 | 1/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0116379 A1 | 5/2012 | Yates et al. |
| 2013/0023868 A1 | 1/2013 | Worrell et al. |
| 2013/0030428 A1 | 1/2013 | Worrell et al. |

OTHER PUBLICATIONS

U.S. Appl. No. 61/550,768, filed Oct. 24, 2011.
International Search Report dated Nov. 27, 2014 for Application No. PCT/US2014/017111, 6 pages.
International Written Opinion dated Nov. 27, 2014 for Application No. PCT/US2014/017111, 8 pages.

* cited by examiner

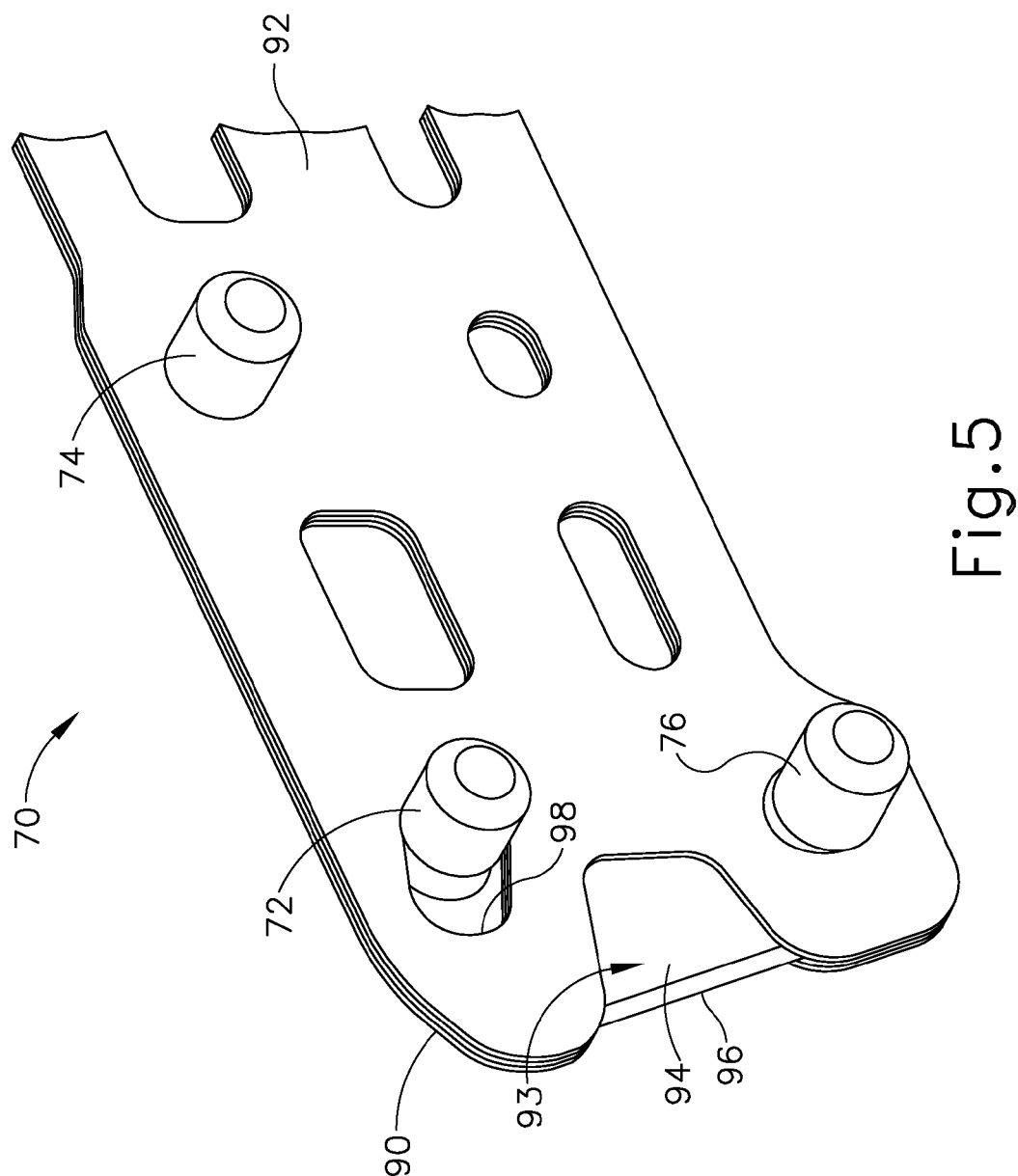

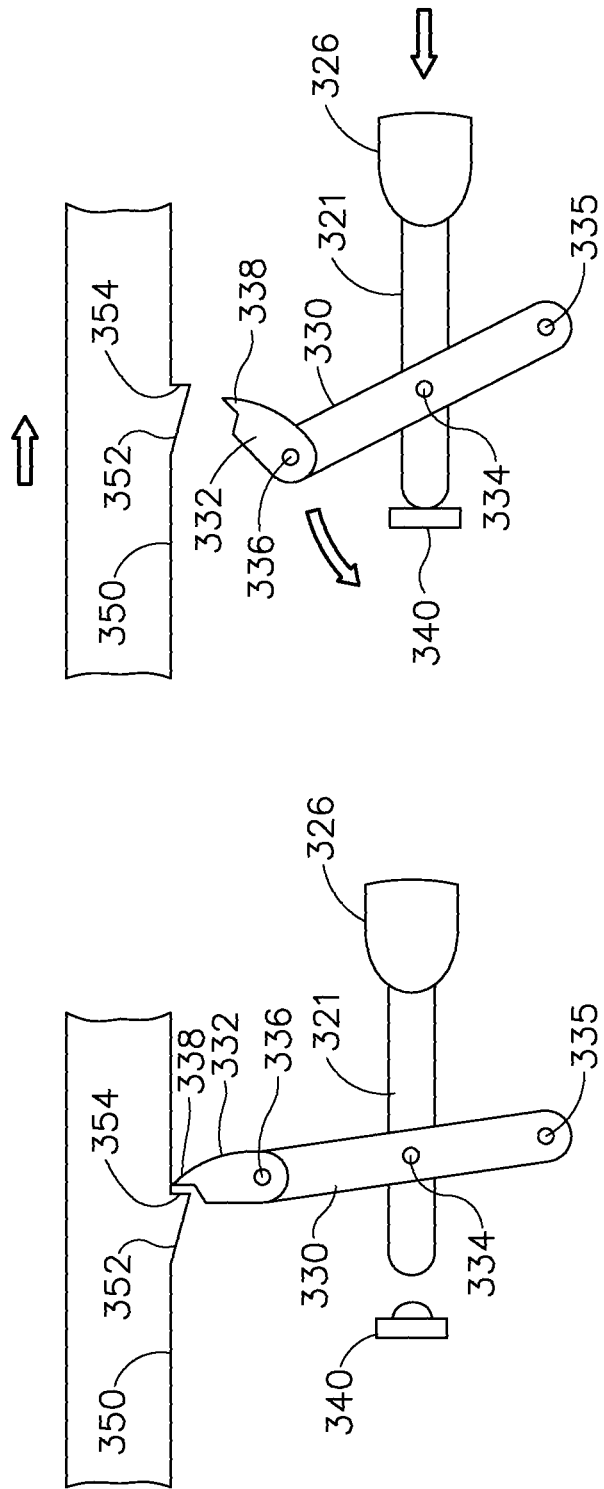

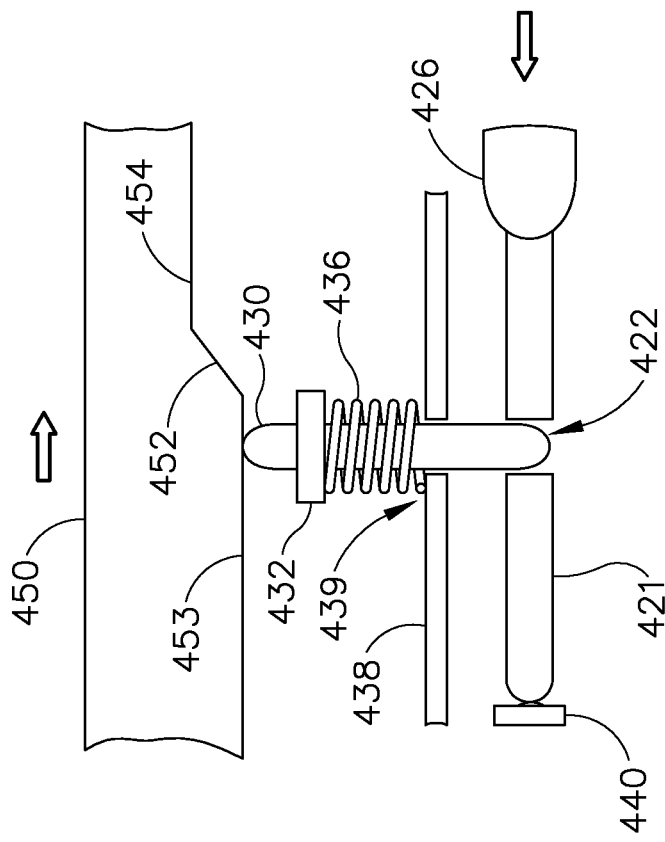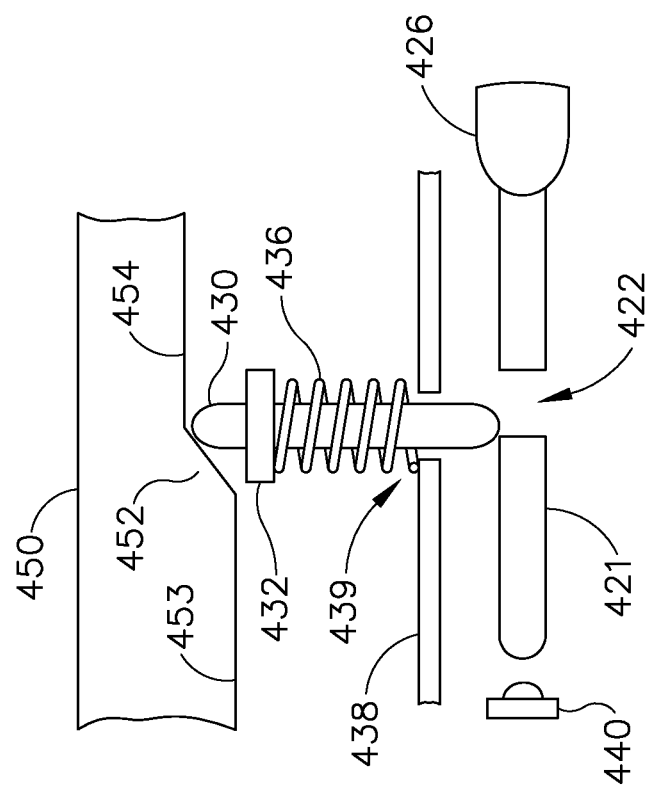

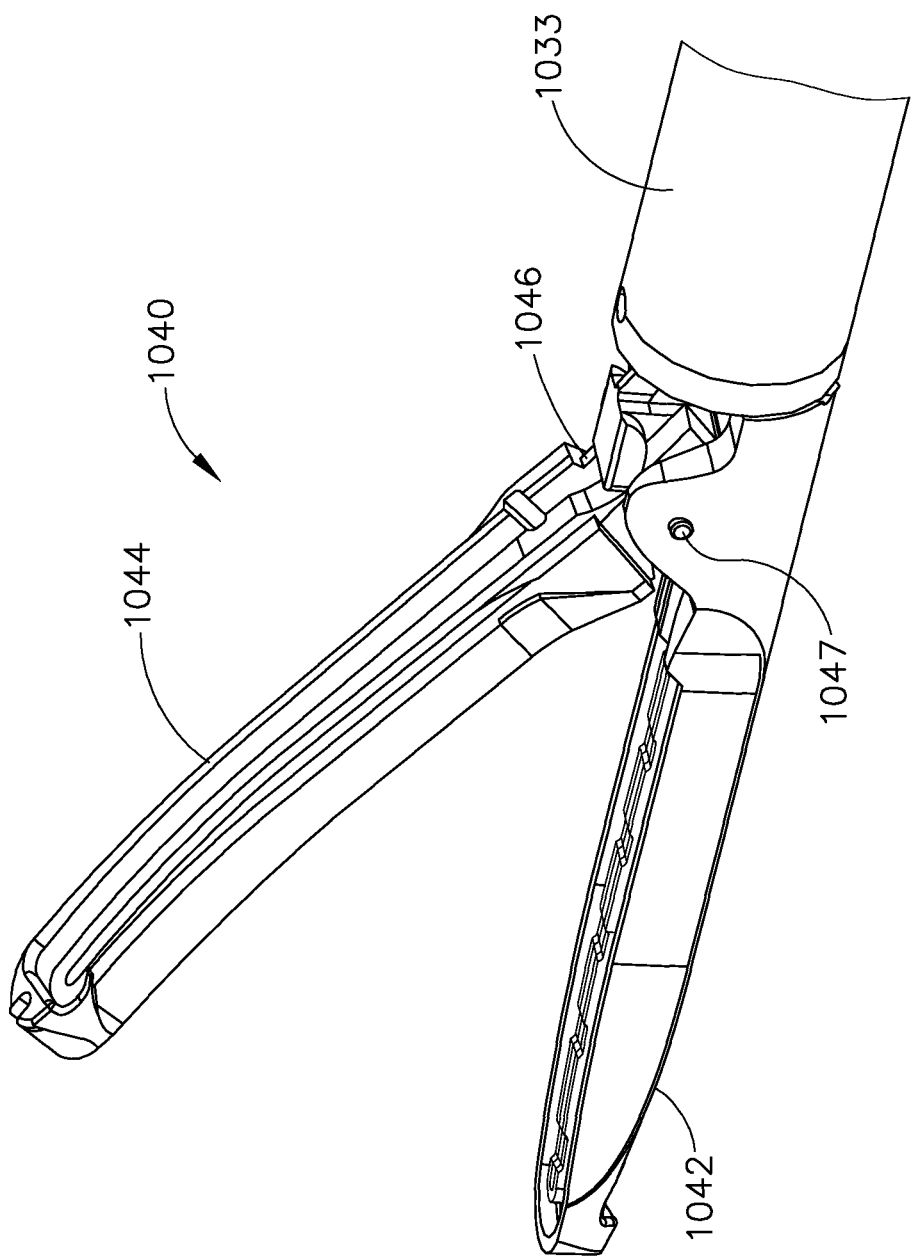

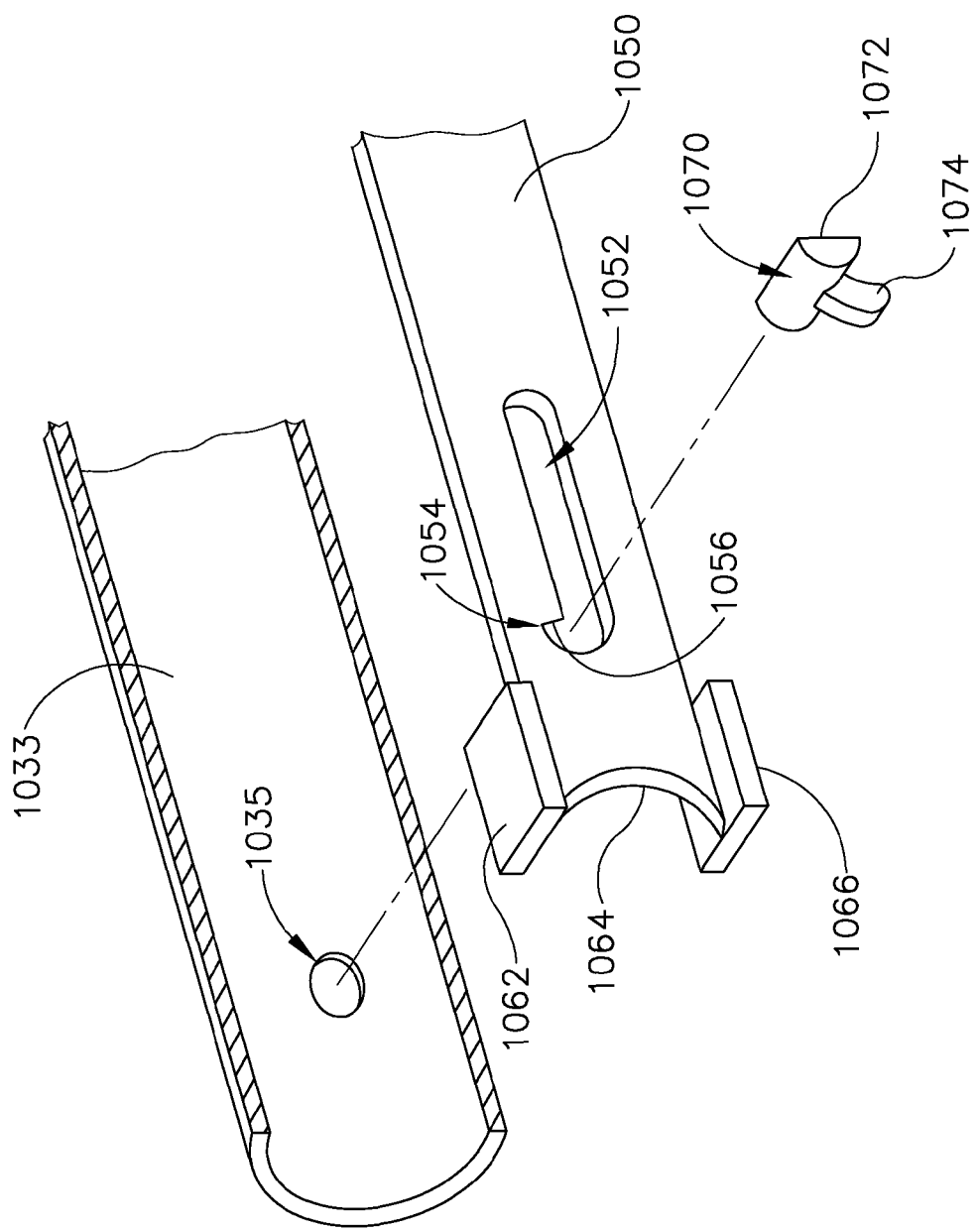

SURGICAL INSTRUMENT WITH PARTIAL TRIGGER LOCKOUT

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011 issued as U.S. Pat. No. 8,939,974 on Jan. 27, 2015), the disclosure of which is incorporated by reference herein; U.S. Pub. No. 2012/0083783, entitled "Surgical Instrument with Jaw Member," published Apr. 5, 2012 (issued as U.S. Pat. No. 8,888,809 on Nov. 18, 2014), the disclosure of which is incorporated by reference herein; U.S. Pub. No. 2012/0116379, entitled "Motor Driven Electrosurgical Device with Mechanical and Electrical Feedback," published May 10, 2012 (issued as U.S. Pat. No. 9,161,803 on Oct. 27, 2015), the disclosure of which is incorporated by reference herein; U.S. Pub. No. 2012/0078243, entitled "Control Features for Articulating Surgical Device," published Mar. 29, 2012 (currently pending), the disclosure of which is incorporated by reference herein; U.S. Pub. No. 2012/0078247, entitled "Articulation Joint Features for Articulating Surgical Device," published Mar. 29, 2012 (currently pending), the disclosure of which is incorporated by reference herein; U.S. Pub. No. 2013/0030428, entitled "Surgical Instrument with Multi-Phase Trigger Bias," published Jan. 31, 2013 (issued as U.S. Pat. No. 9,089,327 on Jul. 28, 2015), the disclosure of which is incorporated by reference herein; and U.S. Pub. No. 2013/0023868, entitled "Surgical Instrument with Contained Dual Helix Actuator Assembly," published Jan. 31, 2013 (currently pending), the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 5 depicts a partial perspective view of the distal end of an exemplary alternative firing beam suitable for incorporation in the instrument of FIG. 1;

FIG. 7A depicts a partial side elevational view of an exemplary trigger lockout assembly for incorporation in the handpiece of FIG. 6A, in a locked position;

FIG. 7B depicts a partial side elevational view of the trigger lockout assembly of FIG. 7A, in an unlocked position;

FIG. 8A depicts a partial side elevational view of another exemplary trigger lockout assembly for incorporation in the handpiece of FIG. 6A, in a locked position;

FIG. 8B depicts a partial side elevational view of the trigger lockout assembly of FIG. 8A, in an unlocked position;

FIG. 22 depicts a perspective view of another exemplary end effector for use with the instrument of FIG. 1;

FIG. 23 depicts an exploded perspective view of distal portions of a firing beam and closure tube of the end effector of FIG. 22, with the closure tube shown in cross-section, and with a coupling pin;

Figure 1:
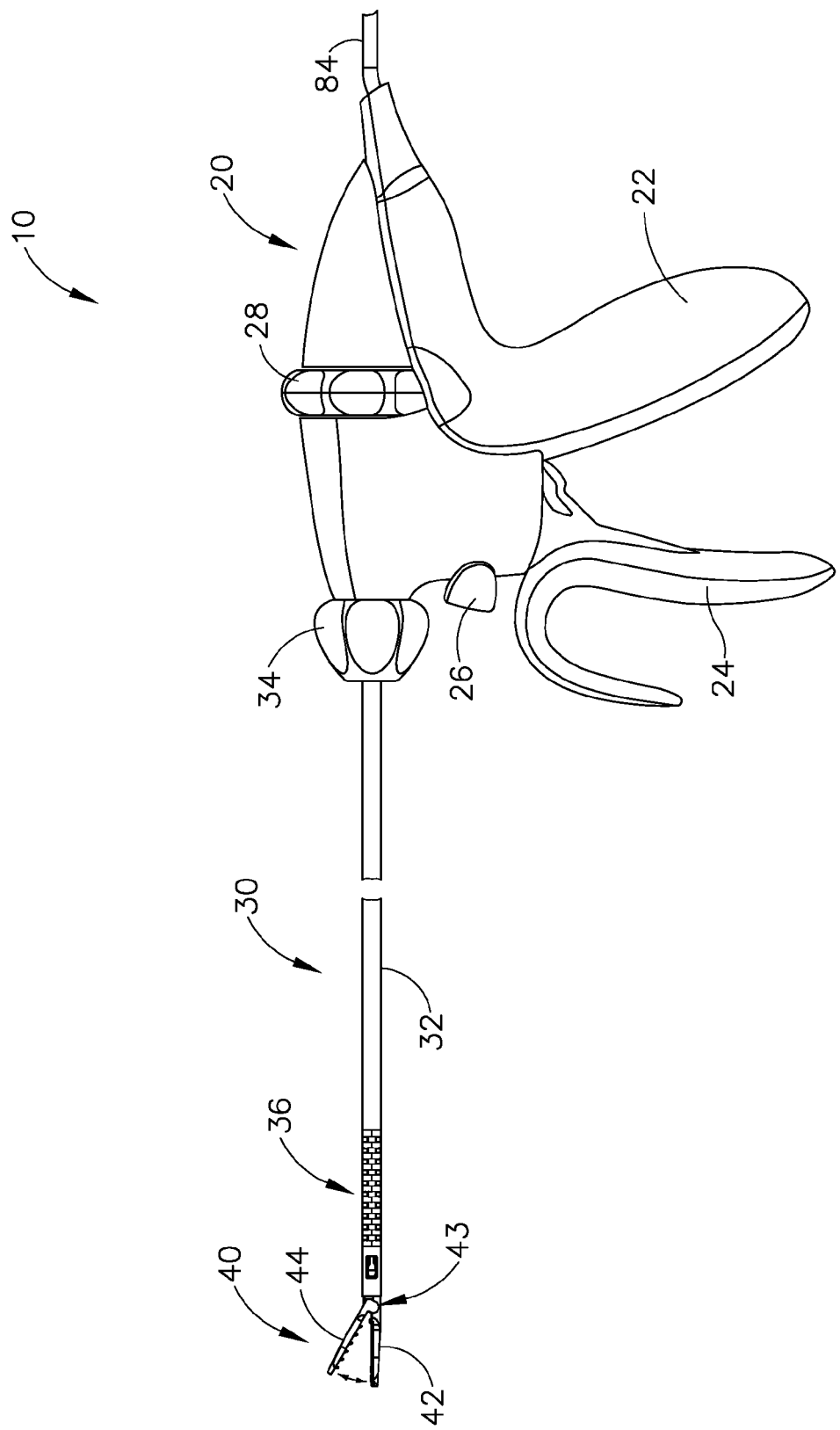
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Electrosurgical Device with Articulation Feature

FIGS. 1-4 show an exemplary electrosurgical instrument (10) that is constructed and operable in accordance with at least some of the teachings of U.S. Pat. Nos. 6,500,176; 7,112,201 7,125,409; 7,169,146; 7,186,253; 7,189,233; 7,220,951; 7,309,849; 7,311,709; 7,354,440; 7,381,209; U.S. Pub. No. 2011/0087218 (issued as U.S. Pat. No. 8,939,974 on Jan. 27, 2015); U.S. Pub. No. 2012/0083783 (issued as U.S. Pat. No. 8,888,809 on Nov. 18, 2014); U.S. Pub. No. 2012/0116379, (issued as U.S. Pat. No. 9,161,803 on Oct. 27, 2015); U.S. Pub. No. 2012/0078243 (currently pending); U.S. Pub. No. 2012/0078247 (currently pending); U.S. Pub. No. 2013/0030428 (issued as U.S. Pat. No. 9,089,327 on Jul. 28, 2015; and/or U.S. Pub. No. 2013/0023868 (currently pending). As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes a rigid outer sheath (32) and an articulation section (36). Articulation section (36) is operable to selectively laterally deflect end effector (40) at various angles relative to the longitudinal axis defined by sheath (32). In some versions, articulation section (36) and/or some other portion of outer sheath (32) includes a flexible outer sheath (e.g., a heat shrink tube, etc.) disposed about its exterior. Articulation section (36) of shaft (30) may take a variety of forms. By way of example only, articulation section (36) may be configured in accordance with one or more teachings of U.S. Pub. No. 2012/0078247 (currently pending), the disclosure of which is incorporated by reference herein. As another merely illustrative example, articulation section (36) may be configured in accordance with one or more teachings of U.S. Pub. No. 2012/0078248 (currently pending), entitled "Articulation Joint Features for Articulating Surgical Device," published Mar. 29, 2012, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating articulation section (36) or any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating articulation section (36) or any portion of shaft (30) that is proximal of articulation section (36). Other suitable rotation schemes will be apparent to those of ordinary skill in the art in view of the teachings herein. Of course, rotatable features may simply be omitted if desired.

Articulation control (28) of the present example is operable to selectively control articulation section (36) of shaft (30), to thereby selectively laterally deflect end effector (40) at various angles relative to the longitudinal axis defined by shaft (30). While articulation control (28) is in the form of a rotary dial in the present example, it should be understood that articulation control (28) may take numerous other forms. By way of example only, some merely illustrative forms that articulation control (28) and other components of handpiece (20) may take are disclosed in U.S. Pub. No. 2012/0078243, (currently pending) the disclosure of which is incorporated by reference herein;in U.S. Pub. No. 2012/0078244 (currently pending), entitled "Control Features for Articulating Surgical Device," published Mar. 29, 2012, the disclosure of which is incorporated by reference herein; and in U.S. Pub. No. 2013/0023868 (currently pending), the disclosure of which is incorporated by reference herein. Still other suitable forms that articulation control (28) may take will be apparent to those of ordinary skill in the art in view of the teachings herein. It should also be understood that some versions of instrument (10) may simply lack an articulation control (28).

B. Exemplary End Effector

End effector (40) of the present example comprises a first jaw (42) and a second jaw (44). In the present example, first jaw (42) is substantially fixed relative to shaft (30); while second jaw (44) pivots relative to shaft (30), toward and away from first jaw (42). Use of the term "pivot" should not be read as necessarily requiring pivotal movement about a fixed axis. In some versions, second jaw (44) pivots about an axis that is defined by a pin (or similar feature) that slides along an elongate slot or channel as second jaw (44) moves toward first jaw (42). In such versions, the pivot axis translates along the path defined by the slot or channel while second jaw (44) simultaneously pivots about that axis. It should be understood that such sliding/translating pivotal movement is encompassed within terms such as "pivot," "pivots," "pivotal," "pivotable," "pivoting," and the like. Of course, some versions may provide pivotal movement of second jaw (44) about an axis that remains fixed and does not translate within a slot or channel, etc.

In some versions, actuators such as rods or cables, etc., may extend through sheath (32) and be joined with second jaw (44) at a pivotal coupling (43), such that longitudinal movement of the actuator rods/cables/etc. through shaft (30) provides pivoting of second jaw (44) relative to shaft (30) and relative to first jaw (42). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
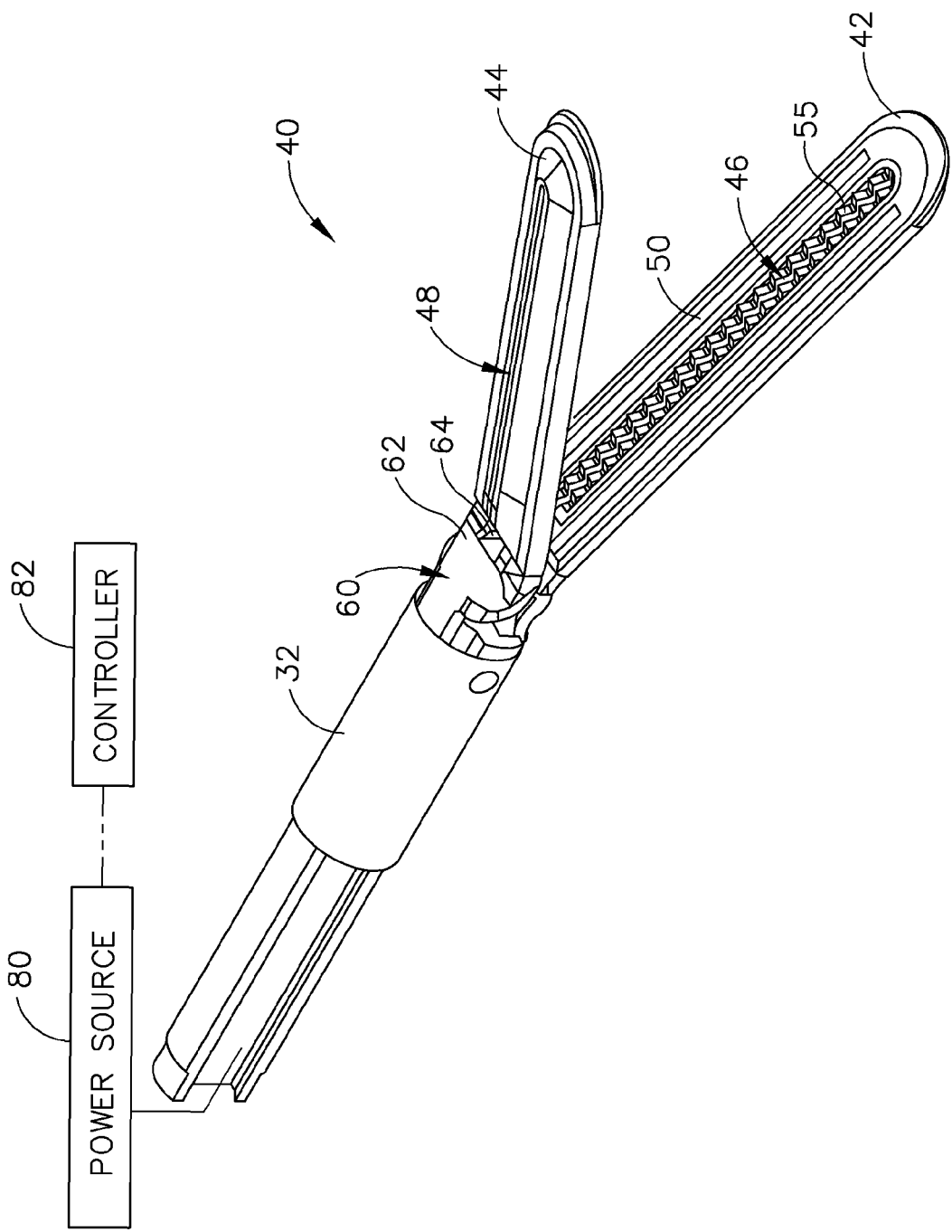
FIG. 2 depicts a perspective view of the end effector of the instrument of FIG. 1, in an open configuration.
Figure 3:
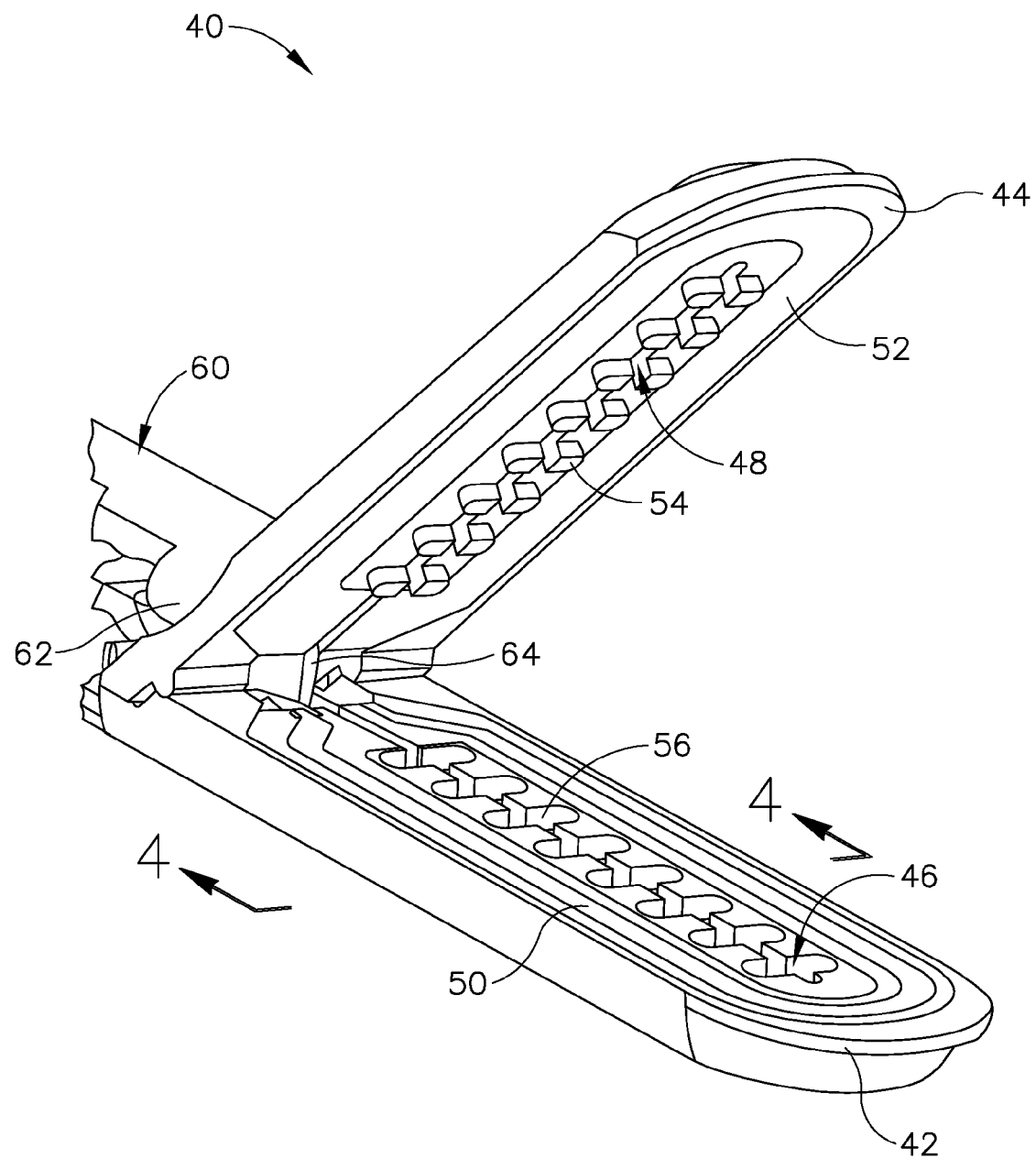
FIG. 3 depicts another perspective view of the end effector of the instrument of FIG. 1, in an open configuration.
Figure 4:
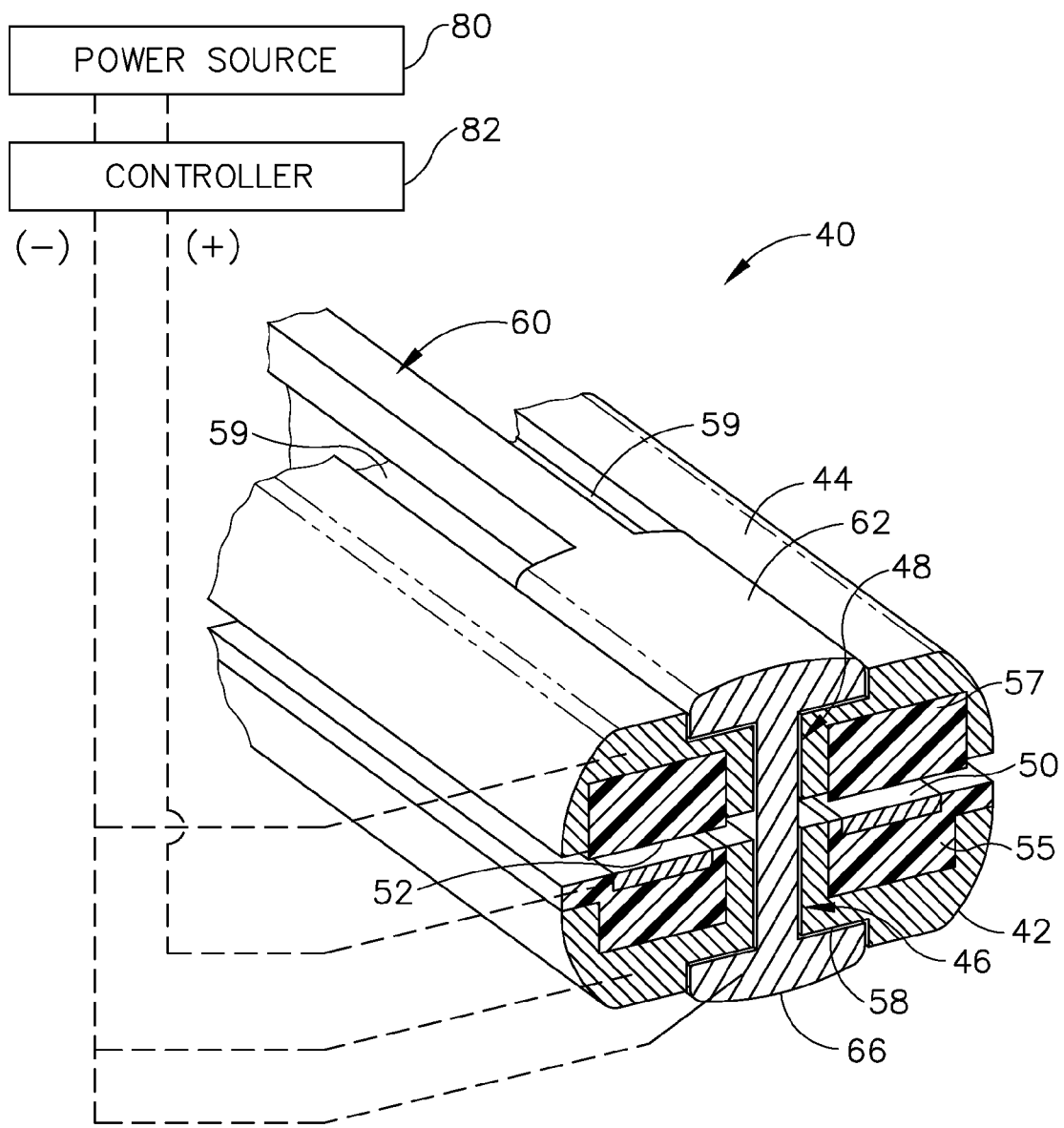
FIG. 4 depicts a cross-sectional end view of the end effector of FIG. 2, in a closed configuration and with the blade in a distal position, taken along line 4-4 of FIG. 3.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). These conductors are coupled with electrical source (80) and a controller (82) via a cable (84), which extends proximally from handpiece (20). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

By way of example only, power source (80) and/or controller (82) may be configured in accordance with at least some of the teachings of U.S. Provisional Pat. App. No. 61/550,768 (abandoned), entitled "Medical Instrument," filed Oct. 24, 2011, the disclosure of which is incorporated by reference herein; U.S. Pub. No. 2011/0082486 (issued as U.S. Pat. No. 9,089,360 on Jul. 27, 2015), entitled "Devices and Techniques for Cutting and Coagulating Tissue," published Apr. 7, 2011, the disclosure of which is incorporated by reference herein; U.S. Pub. No. 2011/0087212 (issued as U.S. Pat. No. 8,986,302 on Mar. 24, 2015), entitled "Surgical Generator for Ultrasonic and Electrosurgical Devices," published Apr. 14, 2011, the disclosure of which is incorporated by reference herein; U.S. Pub. No. 2011/0087213 (issued as U.S. Pat. No. 8,951,248 on Feb. 10, 2015), entitled "Surgical Generator for Ultrasonic and Electrosurgical Devices," published Apr. 14, 2011, the disclosure of which is incorporated by reference herein; U.S. Pub. No. 2011/0087214 (issued as U.S. Pat. No. 9,039,695 on May 26, 2015), entitled "Surgical Generator for Ultrasonic and Electrosurgical Devices," published Apr. 14, 2011, the disclosure of which is incorporated by reference herein; U.S. Pub. No. 2011/0087215 (issued as U.S. Pat. No. 9,050,093 on Jun. 9, 2015), entitled "Surgical Generator for Ultrasonic and Electrosurgical Devices," published Apr. 14, 2011, the disclosure of which is incorporated by reference herein; U.S. Pub. No. 2011/0087216 (issued as U.S. Pat. No. 8,956,349 on Feb. 17, 2015), entitled "Surgical Generator for Ultrasonic and Electrosurgical Devices," published Apr. 14, 2011, the disclosure of which is incorporated by reference herein; and/or U.S. Pub. No. 2011/0087217 (issued as U.S. Pat. No. 9,060,776 on Jun. 23, 2015), entitled "Surgical Generator for Ultrasonic and Electrosurgical Devices," published Apr. 14, 2011, the disclosure of which is incorporated by reference herein. Other suitable configurations for power source (80) and controller (82) will be apparent to those of ordinary skill in the art in view of the teachings herein.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. In other words, it should be understood that serrations may be generally blunt or otherwise atraumatic. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. In some versions, a proximal end of firing beam (60) is secured to a firing tube or other structure within shaft (30); and the firing tube or other structure extends through the remainder of shaft (30) to handpiece (20) where it is driven by movement of trigger (24). Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze trigger (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (44) when firing beam (60) is retracted to a proximal position and to hold jaw (44) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

FIG. 5 shows an exemplary alternative firing beam (70), which may be readily substituted for firing beam (60). In this example, firing beam (70) comprises a blade insert (94) that is interposed between two beam plates (90, 92). Blade insert (94) includes a sharp distal edge (96), such that blade insert (94) will readily sever tissue that is captured between jaws (42, 44). Sharp distal edge (96) is exposed by a proximally extending recess (93) formed in plates (90, 92). A set of pins (72, 74, 76) are transversely disposed in plates (90, 92). Pins (72, 74) together effectively serve as substitutes for upper flange (62); while pin (76) effectively serves as a substitute for lower flange (66). Thus, pins (72, 74) bear against channel (59) of jaw (44), and pin (76) bears against channel (58) of jaw (42), as firing beam (70) is translated distally through slots (46, 48). Pins (72, 74, 76) of the present example are further configured to rotate within plates (90, 92), about the axes respectively defined by pins (72, 74, 76). It should be understood that such rotatability of pins (72, 74, 76) may provide reduced friction with jaws (42, 44), thereby reducing the force required to translate firing beam (70) distally and proximally in jaws (42, 44). Pin (72) is disposed in an angled elongate slot (98) formed through plates (90, 92), such that pin (72) is translatable along slot (98). In particular, pin (72) is disposed in the proximal portion of slot (98) as firing beam

(70) is being translated distally. When firing beam (70) is translated proximally, pin (72) slides distally and upwardly in slot (98), increasing the vertical separation between pins (72, 76), which in turn reduces the compressive forces applied by jaws (42, 44) and thereby reduces the force required to retract firing beam (70). Of course, firing beam (70) may have any other suitable configuration. By way of example only, firing beam (70) may be configured in accordance with at least some of the teachings of U.S. Pub. No. 2012/0083783 (issued as U.S. Pat. No. 8,888,809 on Nov. 18, 2014), the disclosure of which is incorporated by reference herein.

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (42) toward jaw (44) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52). Other suitable ways in which instrument (10) may be operable and operated will be apparent to those of ordinary skill in the art in view of the teachings herein.

II. Exemplary Instrument with a Seal Only Mode

In some instances, it may be desirable to close jaws (42, 44) and activate electrode surfaces (50, 52) with bipolar energy prior to advancing firing beam (60) to sever tissue positioned between jaws (42, 44). This may provide a seal only mode such that the tissue positioned between jaws (42, 44) is sealed prior to or without severing the tissue. Accordingly, features may be incorporated within instrument (10) to close jaws (42, 44) prior to advancing firing beam (60) to sever tissue positioned between jaws (42, 44). The examples below include several merely illustrative versions of such features that may be readily introduced to an instrument (10).

A. Exemplary Handpiece Assemblies

Handpiece (20) of instrument (10) may be modified to include features such that jaws (42, 44) of end effector (40) must be fully closed prior to advancing firing beam (60) to sever tissue between jaws (42, 44). In some instances, it may also be desirable to increase the mechanical advantage to lower the force required to pivot trigger (24) toward pistol grip (22) to advance firing beam (60). The mechanical advantage may also be increased by reducing the distance trigger (24) travels toward pistol grip (22) to advance firing beam (60). The examples below include merely illustrative versions of features that may be readily introduced to a handpiece (20) to increase the mechanical advantage of handpiece (20) in addition ensuring that jaws (42, 44) are fully closed prior to advancement of firing beam (60).

1. Exemplary Sliding Linkage Handpiece Assembly

Figure 6A:
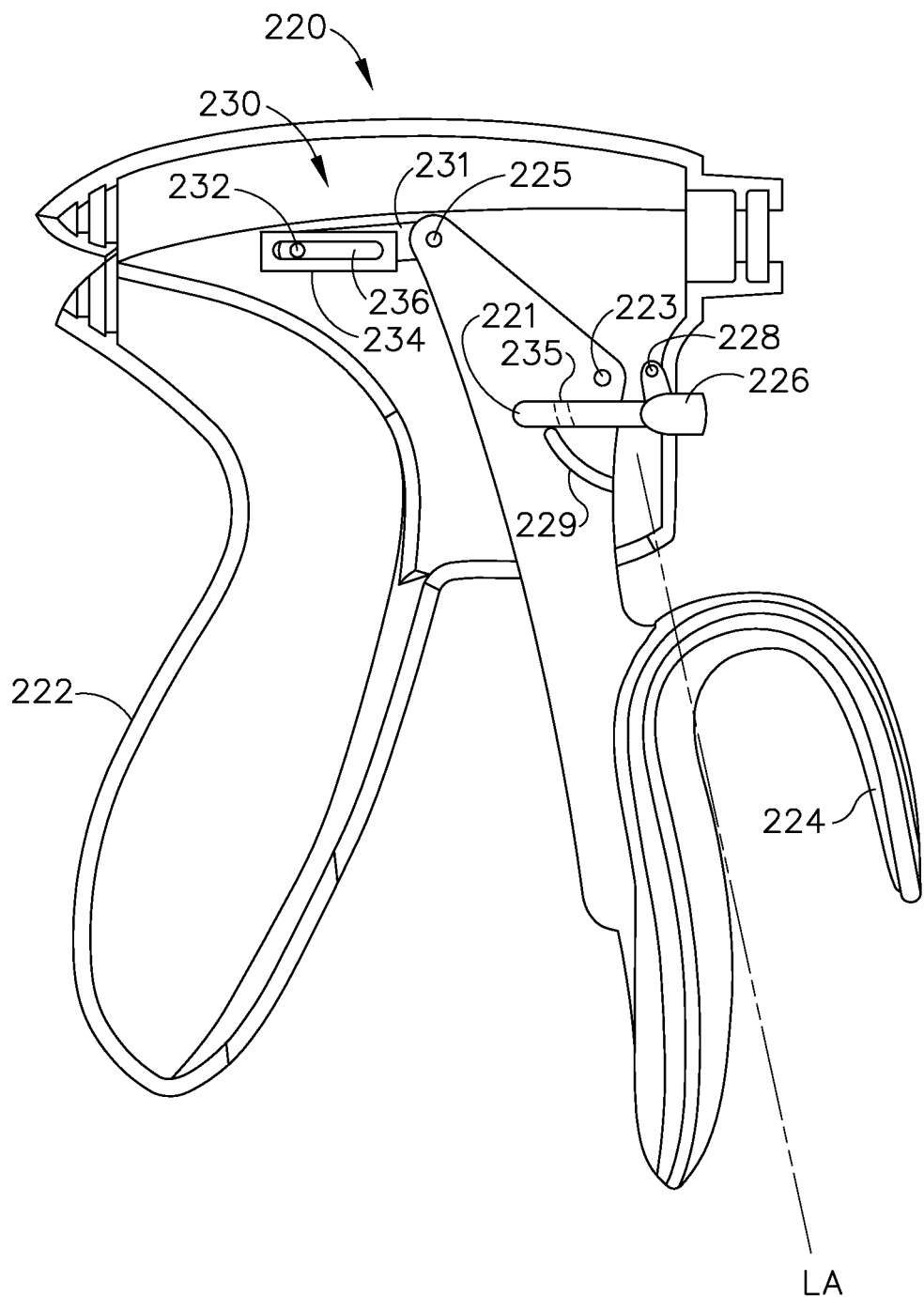
FIG. 6A depicts a partial cross-sectional view of another exemplary handpiece for incorporation in the instrument of FIG. 1, in an initial position.
Figure 6B:
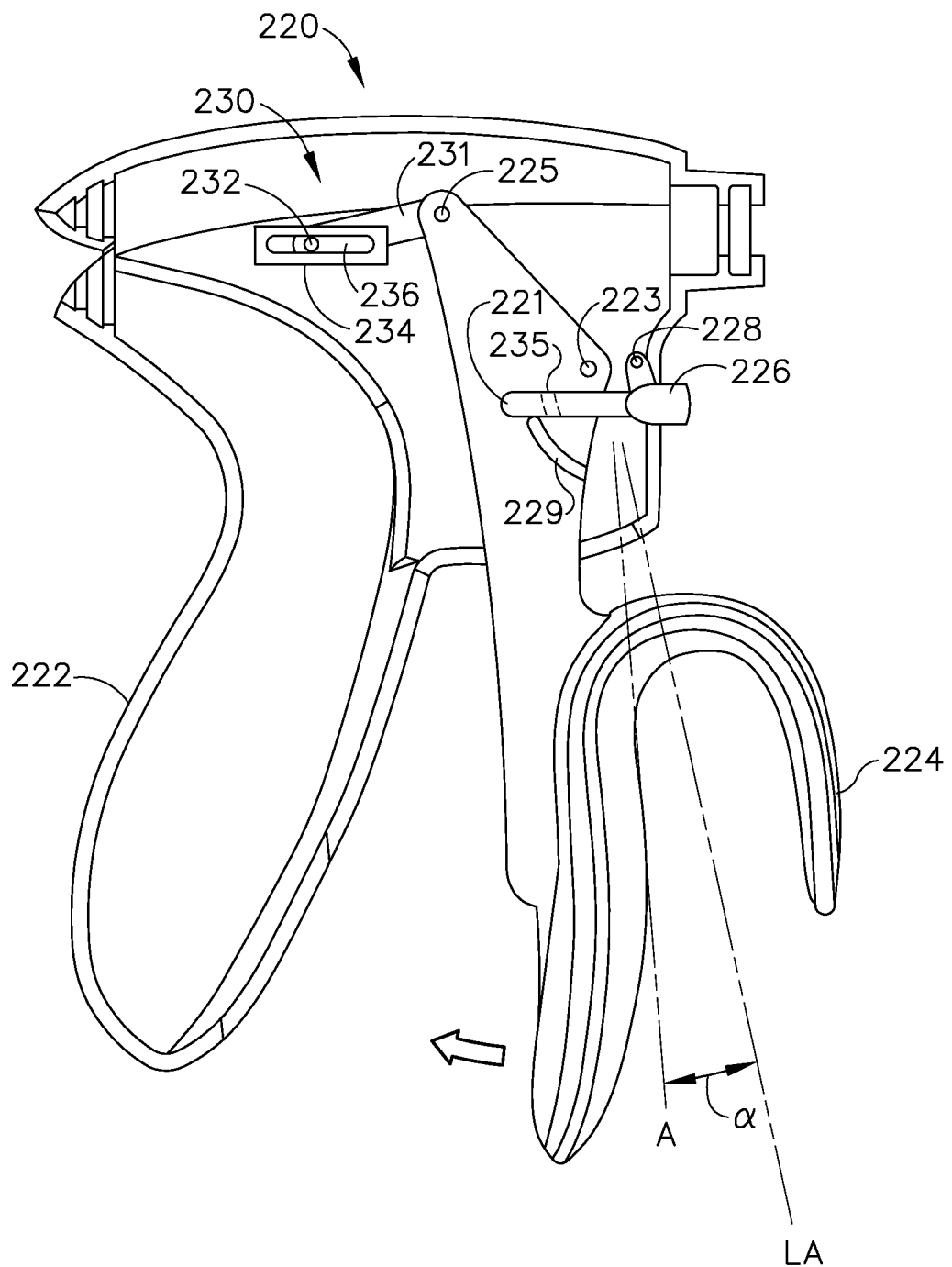
FIG. 6B depicts the handpiece of FIG. 6A, in a second position.
Figure 6C:
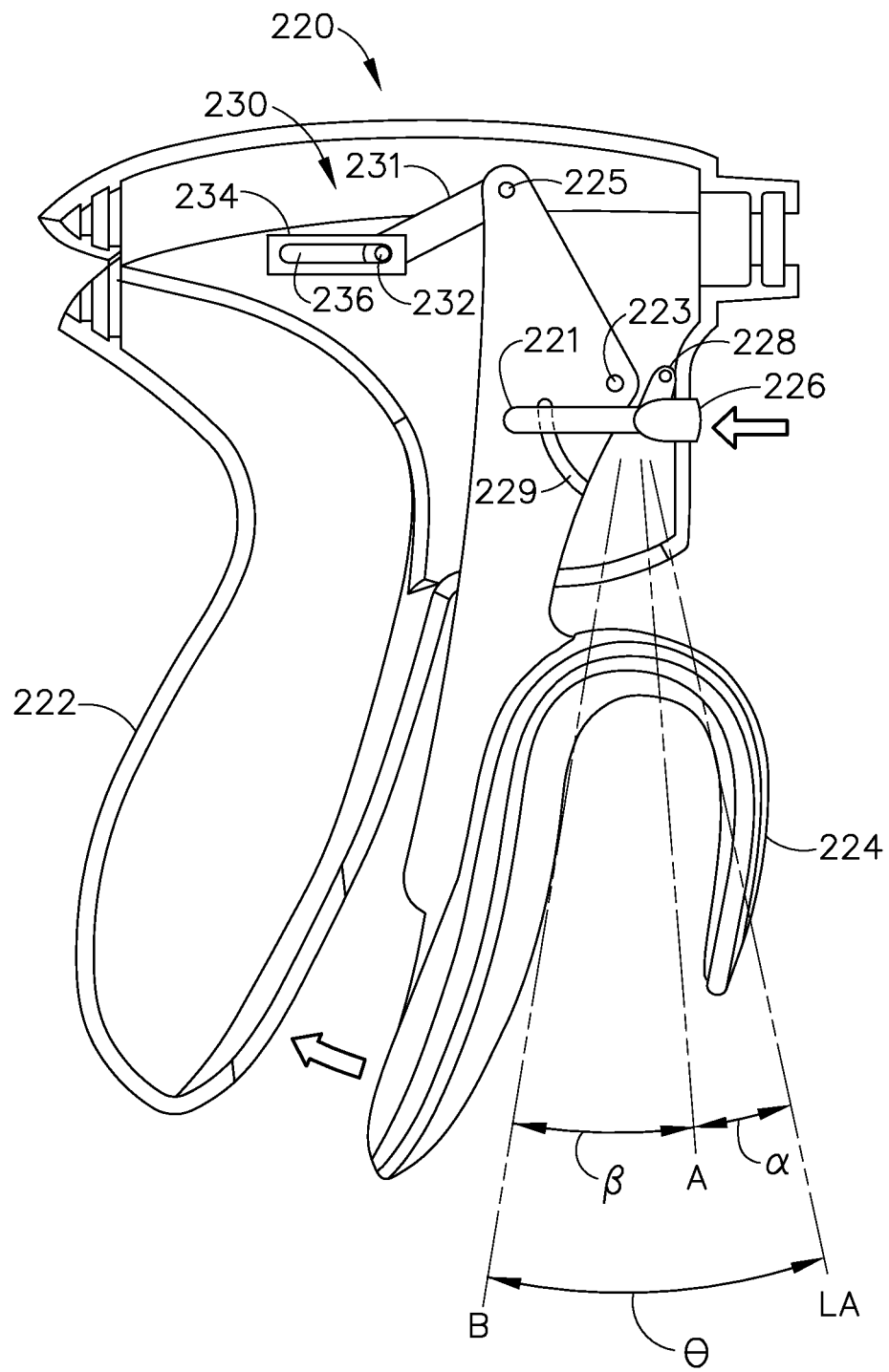
FIG. 6C depicts the handpiece of FIG. 6A, in a fired position.

FIGS. 6A-6C show an exemplary handpiece (220) that may be readily incorporated into instrument (10). Handpiece (220) comprises a pistol grip (222), a trigger (224), a sliding linkage assembly (230), and an activation button (226). Pistol grip (222) is substantially identical to pistol grip (22) of handpiece (20). Trigger (224) is similar to trigger (24), except that trigger (224) is coupled with sliding linkage assembly (230). In the present example, a top portion of trigger (224) is pivotally coupled to sliding linkage assembly (230) via pin (225). Accordingly, as trigger (224) is pivoted toward grip (222) via pin (223), the top portion of trigger (224) pivots to actuate sliding linkage assembly (230) distally. In the present example, the distance from pin (223) to pin (225) is about 1.45 inches, although any of a number of other distances may be provided. Trigger (224) further comprises a rib (229) protruding laterally outwardly from a side wall of trigger (224). In the present example, rib (229) has a curved profile such that rib (229) may slide through a channel (235) of activation button (226) as trigger (224) is pivoted toward grip (222), although any other suitable shape of rib (229) may be used.

Sliding linkage assembly (230) comprises a fixed member (234) with a channel (236) extending through the fixed member (234). Channel (236) is longitudinally aligned with shaft (30) and may be about 0.75 inches in length. Of course, any of a number of other lengths of channel (236) may be provided. A pin (232) is configured to translate within channel (236). Arm (231) couples pin (232) with pin (225) of trigger (224). In the present example, arm (231) is about 1.1 inches long. Of course, any other of a number of lengths of arm (231) may be provided. Accordingly, as trigger (224) is pivoted toward grip (222), trigger pivots pin (225) to thereby pivot arm (231) and translate pin (232) distally within channel (236) of fixed member (234). The proximal end of firing beam (60) is coupled with pin (232) such that firing beam (60) translates within shaft (30) as pin (232) translates within channel (236).

Activation button (226) is similar to activation button (26), except that activation button (226) comprises an arm (221) extending proximally from activation button (226). Arm (221) has a channel (235) extending transversely through arm (221) that is configured to receive rib (229) of trigger (224). Activation button (226) is pivotable relative to handpiece (220) via pin (228). Channel (235) of activation button (226) is offset from rib (229) of trigger (224) until activation button (226) is pivoted relative to handpiece (220). Accordingly, trigger (224) may be pivoted toward grip (222) until rib (229) engages arm (221) of activation button (226). Activation button (226) is then pressed to align channel (235) with rib (229) to allow trigger (224) to continue to pivot toward grip (222).

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Jaws (42, 44) of end effector (40) are opened after manipulating articulation section (36). With jaws (42, 44) open, trigger (224) is at an initial position defining a longitudinal axis (LA), as shown in FIG. 6A. In this initial position, trigger (224) is positioned such that pin (232) is proximally located in channel (236) of fixed member (234). Accordingly, firing beam (60), coupled with pin (232), is also in a proximal position. Activation button (226) is in a distal position such that channel (235) is offset from rib (229) of trigger (224).

Two layers of tissue of the anatomical structure are then captured between jaws (42, 44) by squeezing trigger (224) toward pistol grip (222), as shown in FIG. 6B. Trigger (224) is pivoted to a desired angle (α) to define longitudinal axis (A). The desired angle (α) may be 10 degrees. Of course, any other of a number of angles may be provided. As trigger (224) is pivoted, pin (225) on the top portion of trigger (224) is pivoted distally to pivot arm (231). Arm (231) thereby translates pin (232) within channel (236) to a first distal position. Pin (232) may translate about 0.15 to about 0.20 inches distally within channel (236). Of course, any other of a number of lengths may be provided. In this first distal position, pin (232) translates firing beam (60) distally such that flanges (62, 66) cammingly act to pivot jaw (42) toward jaw (44) to close jaws (42, 44). Rib (229) of trigger (224) contacts arm (221) of activation button (226) such that arm (221) prevents trigger (224) from being pivoted further toward grip (222). Accordingly, firing beam (60) is prevented from being advanced further to sever the tissue captured between jaws (42, 44) until activation button (226) is actuated to provide RF energy to electrode surfaces (50, 52) of end effector (40). However, rib (229) and arm (221) are merely optional. Alternatively, the user may stop squeezing trigger (224) when jaws (42, 44) close. Activation button (226) is then depressed such that electrode surfaces (50, 52) are activated with bipolar RF energy to thermally weld the tissue layer portions captured between jaws (42, 44). Activation button (226) may be depressed prior to pivoting trigger (224) further toward grip (222) such that a seal only mode is provided to thermally weld the tissue between jaws (42, 44) prior to severing the tissue. Trigger (224) may then be released without severing the tissue, or trigger (224) may continue to be advanced to sever the tissue. When activation button (226) is depressed, channel (235) is aligned with rib (229) of trigger (224) to allow trigger (224) to be further pivoted toward grip (222).

With tissue layers captured between jaws (42, 44), firing beam (60) continues to advance distally by the user squeezing trigger (224) further toward pistol grip (222), as shown in FIG. 6C. Trigger (224) is pivoted by an angle (β) to longitudinal axis (B). Angle (β) may be about 10 to about 18 degrees such that the total amount of rotation (θ) by trigger (224) is about 20 to about 28 degrees from longitudinal axis (LA) to longitudinal axis (B). Of course, any other of a number of angles may be provided. When trigger (224) is pivoted further toward grip (222), pin (225) pivots arm (231) and translates pin (232) further distally within channel (236) to a second distal position. Pin (232) may be translated about 0.60 inches from the first distal position to the second distal position. Of course, any other of a number of lengths may be provided. Pin (232) thereby advances firing beam (60) distally. As firing beam (60) continues to advance distally, distal blade (64) simultaneously severs the clamped tissue layers, resulting in separated upper layer portions being apposed with respective separated lower layer portions. Accordingly, firing beam (60) is advanced to sever tissue while activation button (226) is depressed and RF energy is applied to end effector (40).

Trigger (224) is then released to pivot away from grip (222) and return to the position in FIG. 6B. As trigger (224) pivots distally, trigger (224) pivots arm (231) of linkage assembly (230) to thereby translate pin (232) proximally within channel (236) to the first distal position. Accordingly, pin (232) translates firing beam (60) proximally to retract distal blade (64). Rib (229) rotates out of channel (235) of arm (221) such that activation button (226) is released to deactivate the RF energy applied to end effector (40). End effector (40) may then be removed from the patient or repositioned to thermally weld and/or sever additional tissue layers. If end effector (40) is repositioned, trigger (224) is then pivoted further away from grip (220) to the initial position in FIG. 6A. Trigger (224) thereby pivots arm (231) of linkage assembly (230) to translate pin (232) proximally. Pin (232) thereby translates firing beam (60) proximally to open jaws (42, 44) such that additional tissue layers may be thermally welded and/or severed.

In some versions, firing beam (60) may be prevented from advancing distally to sever tissue until activation button (226) is depressed, instead of preventing trigger (224) from pivoting until activation button (226) is depressed. FIGS. 7A-7B show exemplary firing beam (60) lockout features. In the present example, activation button (326) is similar to activation button (226), except that activation button (326) is coupled to a locking linkage (330) via pin (334) such that locking linkage (330) is pivotable relative to arm (321) of activation button (326). A lower portion of locking linkage (330) is coupled with handpiece (220) via pin (335) such that locking linkage (330) is pivotable about pin (335). The top portion of locking linkage (330) is coupled with a locking member (332) via pin (336) such that locking member (332) is pivotable relative to locking linkage (330). Locking member (332) comprises a tip (338) extending outwardly from locking member (332). Tip (338) of locking member (332) is configured to engage firing beam (350). Firing beam (350) is similar to firing beam (60), except that firing beam (350) comprises a protrusion with a distal wall (354) and a ramped wall (352). Distal wall (354) is configured to engage tip (338) of locking member (332).

FIG. 7A shows activation button (326) in an initial position such that activation button (326) is not depressed. In this initial position, arm (321) of activation button (326) is not engaged with switch (340) such that RF energy is not being applied to end effector (40). Locking linkage (330) is positioned transverse to arm (321). Locking member (332) is aligned with locking linkage (330) such that tip (338) is configured to engage distal wall (354) of the protrusion of firing beam (350). Accordingly, distal wall (354) engages tip (338) such that tip (338) prevents firing beam (350) from being advanced distally to sever tissue while activation button (326) is not depressed. Activation button (326) may then be depressed, as shown in FIG. 7B. When activation button (326) is depressed, arm (321) of activation button (326) is translated to press switch (340) and activate RF energy to end effector (40). Arm (321) also pivots locking linkage (330) when arm (321) is translated. When locking linkage (330) is pivoted, locking member (332) also pivots relative to locking linkage (330). This translates tip (338) of locking member (332) to disengage firing beam (350) such that firing beam (350) may continue to be advanced distally to sever tissue captured between jaws (42, 44) of end effector (40).

FIGS. 8A-8B show additional exemplary firing beam lockout features. In the present example, activation button (426) is similar to activation button (226), except that activation button (426) defines an opening (422) in arm (421) of activation button (426). A locking member (430) is positioned transversely above arm (421) of activation button (426). Locking member (430) comprises a flange (432) extending outwardly from locking member (430). A resilient member (436) is positioned around locking member (430) between flange (432) and a wall (438) coupled with handpiece (220). Resilient member (436) biases locking member (430) upwardly. Wall (438) defines an opening (439) to receive locking member (430). The top portion of locking member (430) engages firing beam (450). Firing beam (450) is similar to firing beam (60), except that firing beam (450) comprises a ramped surface (452) that connects proximal portion (453) of firing beam (450) to distal portion (454) of firing beam (450). Proximal portion (453) of firing beam (450) has a greater height than distal portion (454) of firing beam.

FIG. 8A shows activation button (426) in an initial position such that activation button (426) is not depressed. In this initial position, arm (421) of activation button (326) is not engaged with switch (440) such that RF energy is not being applied to end effector (40). Locking member (430) is positioned transversely above arm (421). Opening (422) of activation button (426) is offset from locking member (430) such that locking member (430) is prevented from translating downwardly through opening (422). The top portion of locking member (430) engages distal portion (454) of firing beam (450). Ramped surface (452) prevents firing beam (450) from translating distally past locking member (430). This prevents firing beam (450) from being advanced distally to sever tissue while activation button (426) is not depressed. Of course, firing beam (450) may be translated far enough to close jaws (42, 44) before reaching this lockout stage. Activation button (426) may then be depressed, as shown in FIG. 8B. When activation button (426) is depressed, arm (421) of activation button (426) is translated to press switch (440) and activate RF energy to end effector (40). When arm (421) is translated, opening (422) of arm (421) is aligned with locking member (430). This allows firing beam (450) to be translated distally such that ramped surface (452) cammingly pushes locking member (430) through opening (422) of arm (421). Firing beam (550) may continue to be advanced distally to sever tissue captured between jaws (42, 44) of end effector (40).

2. Exemplary Dual Cam Handpiece Assembly

Figure 9A:
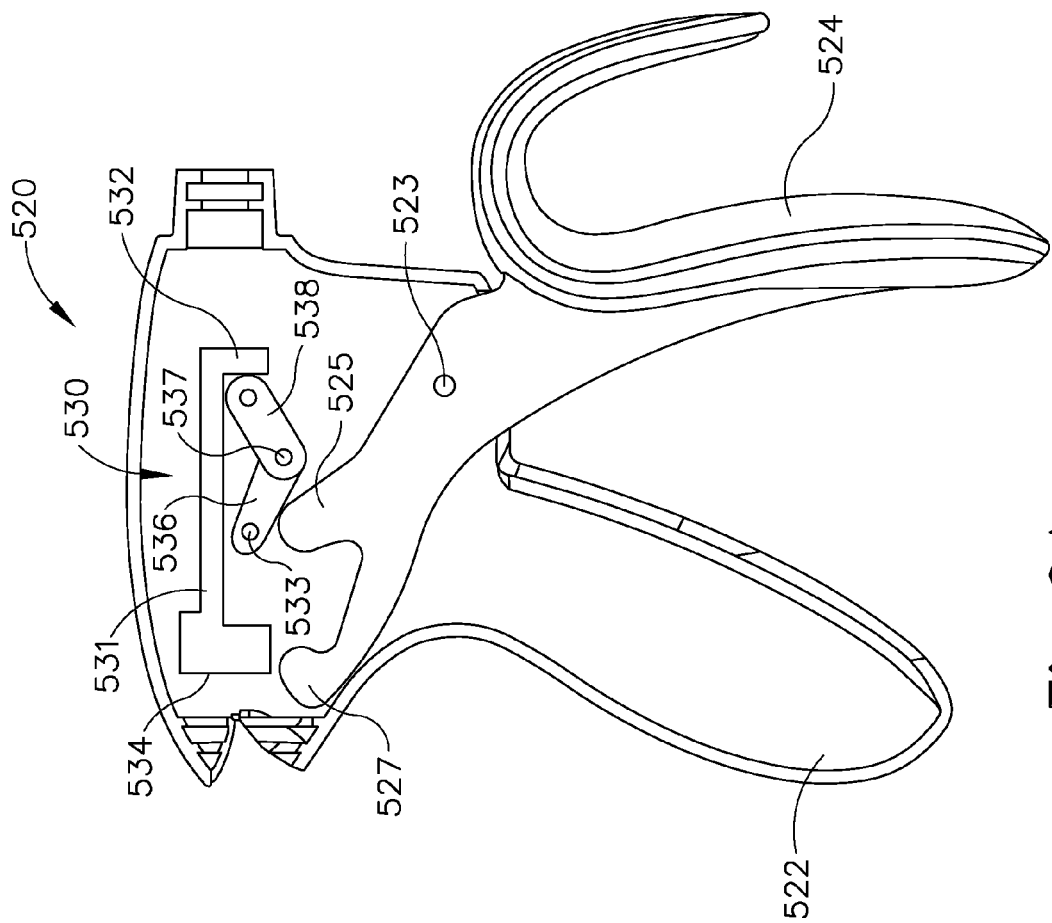
FIG. 9A depicts a partial cross-sectional view of another exemplary handpiece for incorporation in the instrument of FIG. 1, in an initial position.
Figure 9B:
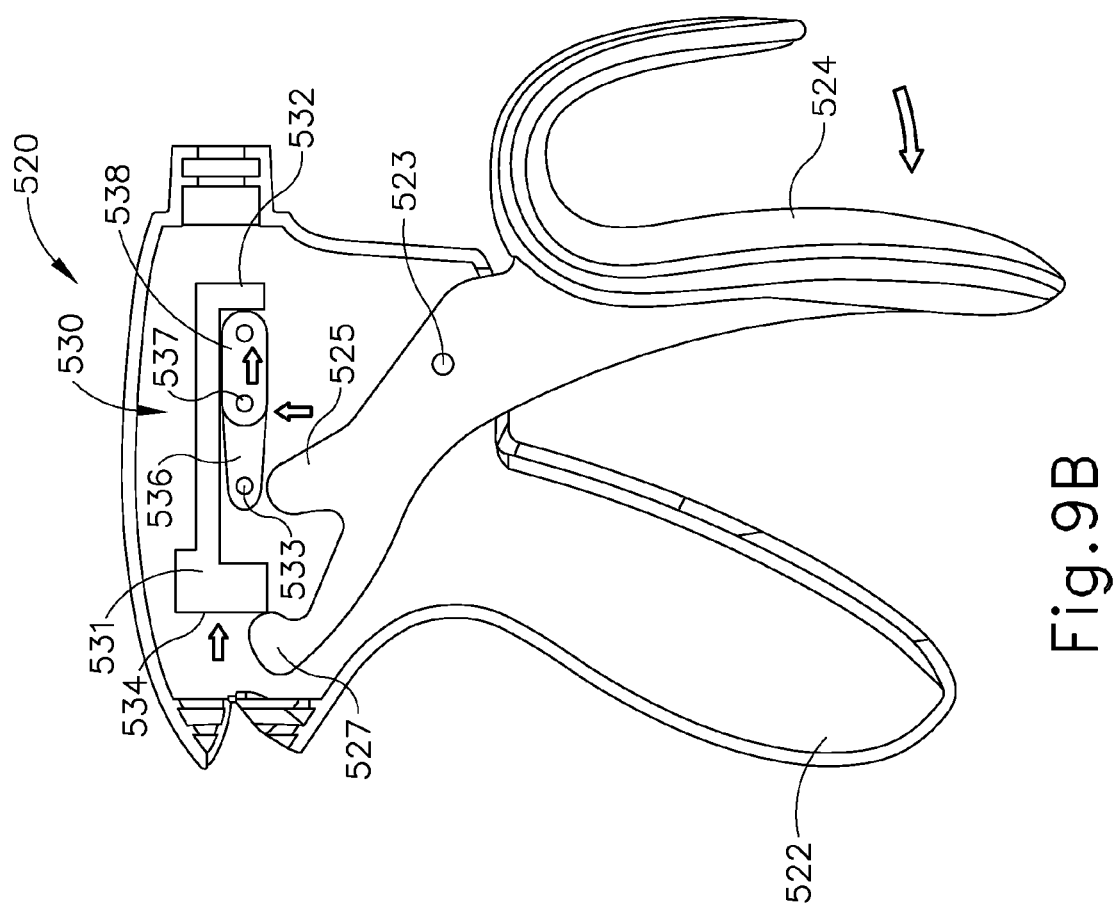
FIG. 9B depicts the handpiece of FIG. 9A, in a second position.
Figure 9C:
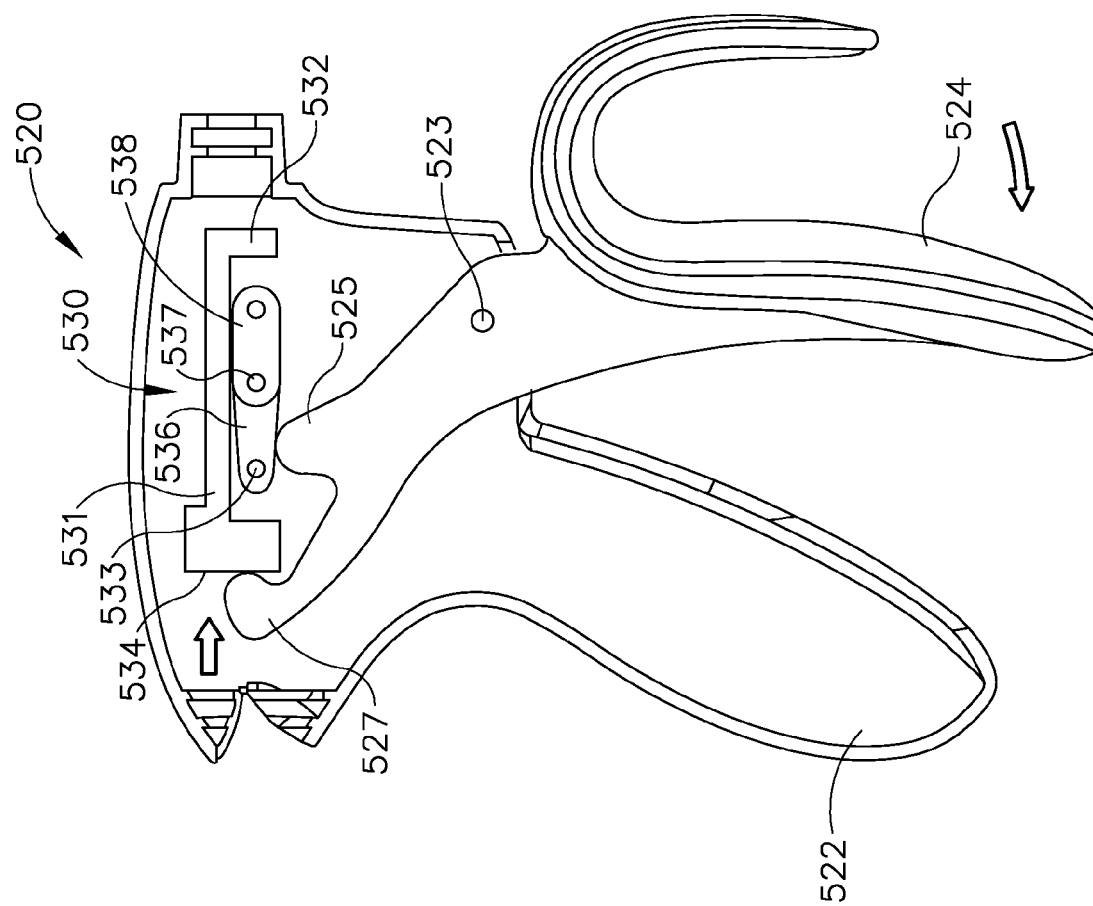
FIG. 9C depicts the handpiece of FIG. 9A, in a fired position.

FIGS. 9A-9C show another exemplary handpiece (520) that is similar to handpiece (20), except that handpiece (520) comprises a dual cam trigger (524). Trigger (524) is similar to trigger (24), except that trigger (524) comprises a first extension (525) and a second extension (527) extending within handpiece (520). Second extension (527) extends proximally from first extension (525). First and second extensions (525, 527) are configured to engage a linkage assembly (530). Linkage assembly (530) comprises a first linkage (536), a second linkage (538), and a translating member (531). First and second linkage (536, 538) are coupled via pin (537) such that first and second linkages (536, 538) are pivotable relative to each other. The opposing end of first linkage (536) is secured to housing (522) of handpiece (520) via pin (533). The opposing end of second linkage (538) is engaged with translating member (531). Translating member (531) comprises a proximal wall (534) extending transversely from the proximal end of translating member (531) and a distal wall (532) extending transversely from the distal end of translating member (531). Translating member (531) is longitudinally aligned with shaft (30) and is translatable within handpiece (520). Distal wall (532) of translating member (531) is coupled with firing beam (60) such that translating member (531) translates firing beam (60).

Trigger (524) is pivoted relative to grip (522) about a pivot pin (523) to actuate firing beam (60), similar to trigger (224) described above. FIG. 9A shows trigger (524) in an initial position. In this initial position, trigger (524) is positioned away from grip (522) such that first extension (525) contacts first linkage (536) and second extension (527) is spaced proximally from proximal wall (534). Translating member (531) is in a proximal position and linkages (536, 538) in a folded configuration. Accordingly, firing beam (60), coupled with translating member (531), is also in a proximal position such that jaws (42, 44) of end effector (40) are open.

Jaws (42, 44) are then closed by squeezing trigger (524) toward pistol grip (522) to a first proximal position, as shown in FIG. 9B. Trigger (524) rotates within handpiece (520) via pin (523). First extension (525) of trigger (524) thereby engages first linkage (536) of linkage assembly (530) and cammingly drives first linkage (536) upwardly. This drives second linkage (538) distally as the folded configuration formed by linkages (536, 538) collapses, which drives translating member (531) and thus firing beam (60) to a first distal position to close jaws (42, 44). Second extension (527) does not drive proximal wall (534) during this range of motion. Trigger (524) may be rotated at an angle of about 10 degrees to translate firing beam (60) about 0.15 to about 0.20 inches. Of course, any other of a number of angles and distances may be provided. Any of the locking features described above may be incorporated into handpiece (520) to prevent trigger (524) from continuing to pivot further toward grip (522) to translate firing beam (60) to sever tissue between jaws (42, 44) until activation button (26) has been pressed. After reaching the stage shown in FIG. 9B, activation button (26) is then depressed such that electrode surfaces (50, 52) are activated with bipolar RF energy to thermally weld the tissue layer portions captured between jaws (42, 44). Trigger (524) may then be released without severing the tissue, or trigger (524) may continue to be pivoted toward grip (522) to sever the tissue.

Trigger (524) may then be pivoted further toward grip (522), as shown in FIG. 9C. As trigger (524) is pivoted to a second proximal position, second extension (527) of trigger (524) engages proximal wall (534) of translating member (531) to drive translating member (531) further distally. Accordingly, translating member (531) pushes firing beam (60) further distally to sever tissue between jaws (42, 44). Trigger (524) may be rotated at an additional angle of about 10 to about 18 degrees to translate firing beam (60) about 0.60 inches to sever tissue. Of course, any other of a number of angles or distances may be provided. Trigger (524) may then be released to return to the initial position of FIG. 9A and return linkage assembly (530) and firing beam (60) to the proximal position to open jaws (42, 44). It should be understood from the foregoing that first extension (525) drives firing beam (60) through a first range of motion via linkages (536, 538) to close jaws (42, 44); while second extension (527) drives firing beam (60) through a second range of motion via proximal wall (534) to sever tissue captured between jaws (42, 44). These staged engagements may provide an increased mechanical advantages of trigger (524) through the advancement stroke of firing beam (60), as compared to a relationship between a conventional trigger and firing beam. For instance, the mechanical advantage may be increased through the jaw closure portion of the stroke and/or through the tissue severing portion of the stroke.

3. Exemplary Rack Handpiece Assembly

Figure 10A:
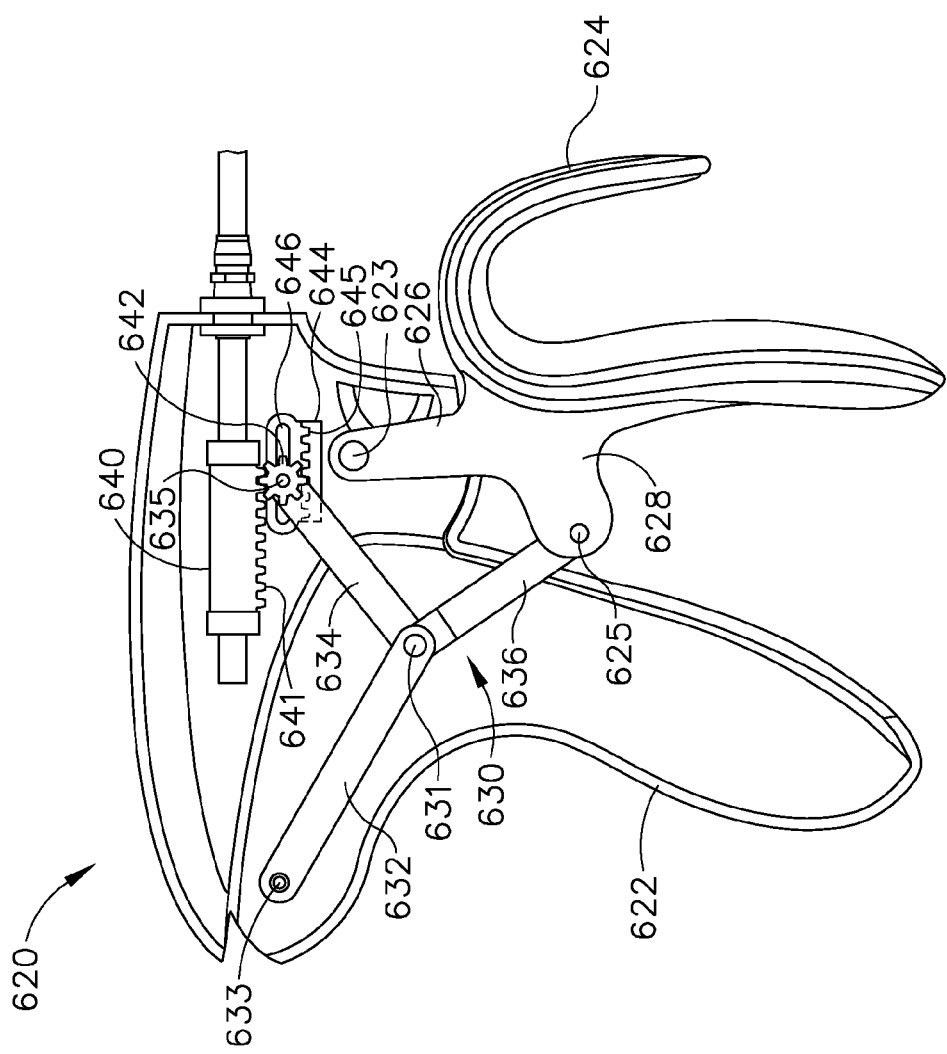
FIG. 10A depicts a partial cross-sectional view of another exemplary handpiece for incorporation in the instrument of FIG. 1, in an initial position.
Figure 10B:
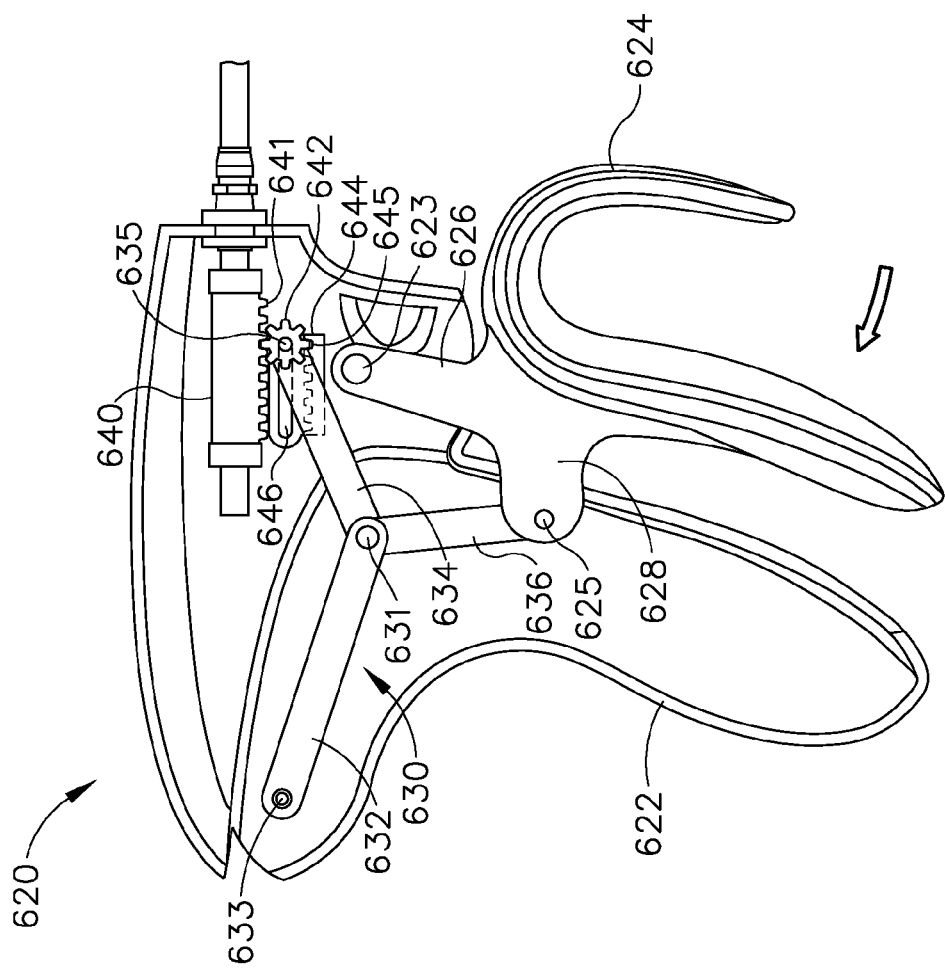
FIG. 10B depicts the handpiece of FIG. 10A, in a fired position.

FIGS. 10A-10B show another exemplary handpiece (620) that is similar to handpiece (20), except that handpiece (620) comprises a linkage assembly (630) and a rack (640). Trigger (624), shown in FIG. 10A, is similar to trigger (24), except that trigger (624) comprises a first extension (626) and a second extension (628). First extension (626) extends from trigger (624) within handpiece (620) and is coupled to handpiece (620) via pin (623) such that trigger (624) is pivotable relative to handpiece (620) via pin (623). Second extension (628) extends proximally from trigger (624) within handpiece (620). Second extension (628) is coupled with linkage assembly (630) via pin (625). Linkage assembly (630) comprises a first linkage (636), a second linkage (632), and a third linkage (634). First linkage (636) is coupled with second extension (628) via pin (625). The opposing end of first linkage (636) is coupled with an end of second linkage (632) and an end of third linkage (634) via pin (631). The other end of second linkage (632) is secured to handpiece (620) via pin (633). The other end of third linkage (634) is coupled with a gear (642) via pin (635). Accordingly, trigger (624) is actuated to pivot linkages (636, 632, 634) to translate and rotate gear (642).

Pin (635) extends through gear (642) to couple gear (642) to fixed member (644). Fixed member (644) defines a channel (646) that is substantially parallel with shaft (30). Pin (635) extends within channel (646) such that pin (635) is translatable within channel (646). Fixed member (644) further comprises a longitudinal row of teeth (645) that are configured to engage the teeth of gear (642). Accordingly, as pin (635) translates within channel (646) of fixed member (644), the teeth of gear (642) engage teeth (645) of fixed member (644) to rotate gear (642) such that gear (642) translates along fixed member (644). Teeth of gear (642) also engage a longitudinal row of teeth (641) of rack (640). Gear (642) thus translates rack (640) as gear (642) translates along fixed member (644). Rack (640) is positioned around firing beam (60) such that rack (640) translates firing beam (60).

Trigger (624) is pivoted relative to grip (622) to actuate firing beam (60). FIG. 10A shows trigger (624) in an initial position. In this initial position, trigger (624) is positioned away from grip (622) such that gear (642) and rack (640) are in a proximal position. Accordingly, firing beam (60), coupled with rack (640), is also in a proximal position such that jaws (42, 44) of end effector (40) are open. Jaws (42, 44) are then closed by squeezing trigger (624) toward pistol grip (622), as shown in FIG. 10B. Trigger (624) rotates within handpiece (620) via pin (623). Second extension (628) of trigger (624) thereby pivots first linkage (636) toward second linkage (632). This pivots third linkage (634) to translate gear (642) distally along fixed member (644). As gear (642) translates along fixed member (644), gear (642) engages teeth (645) of fixed member (644) to rotate gear (642). Gear (642) thereby engages teeth (641) of rack (640) to translate rack (640) distally. Gear (642) may drive rack (640) at a distance of 2:1. For instance, gear (642) may translate distally about 0.4 inches to translate rack (640) distally about 0.8 inches. Of course, any other of a number of distances may be provided. Accordingly, rack (640) translates firing beam (60) distally.

As trigger (624) is pivoted toward grip (622), trigger (624) may be stopped at a first position such that trigger (624) is rotated at an angle of about 10 degrees to translate firing beam (60) about 0.15 to about 0.20 inches. Of course, any other of a number of angles and distances may be provided. Any of the locking features described above may be incorporated into handpiece (620) to prevent trigger (624) from continuing to pivot further toward grip (622) to translate firing beam (60) to sever tissue between jaws (42, 44) until activation button (26) has been pressed. Activation button (26) may then be depressed such that electrode surfaces (50, 52) are activated with bipolar RF energy to thermally weld the tissue layer portions captured between jaws (42, 44). Trigger (624) may then be released without severing the tissue, or trigger (624) may continue to be advanced to sever the tissue. Trigger (624) may be rotated at an additional angle of about 10 to about 18 degrees to translate firing beam (60) about 0.60 inches to sever tissue. Of course, any other of a number of angles or distances may be provided. Trigger (624) may then be released to return to the initial position of FIG. 10A and rack (640) and firing beam (60) to the proximal position to open jaws (42, 44).

Figure 11A:
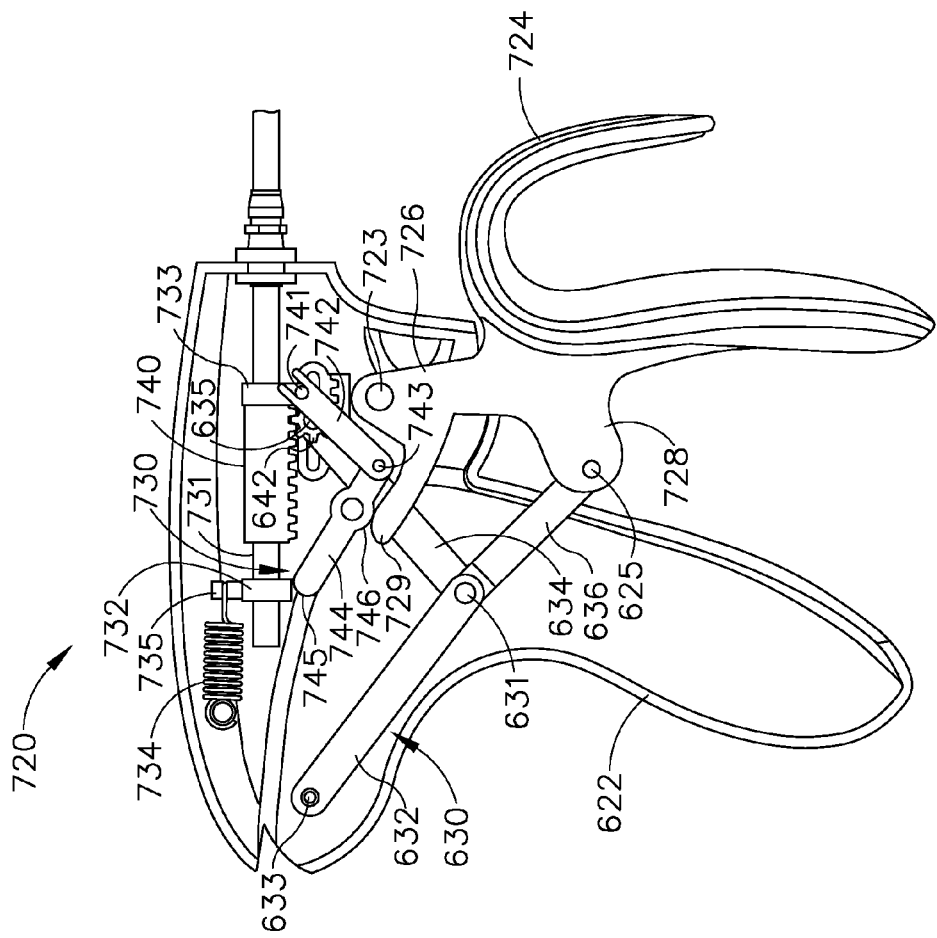
FIG. 11A depicts a partial cross-sectional view of another exemplary handpiece for incorporation in the instrument of FIG. 1, in an initial position.
Figure 11B:
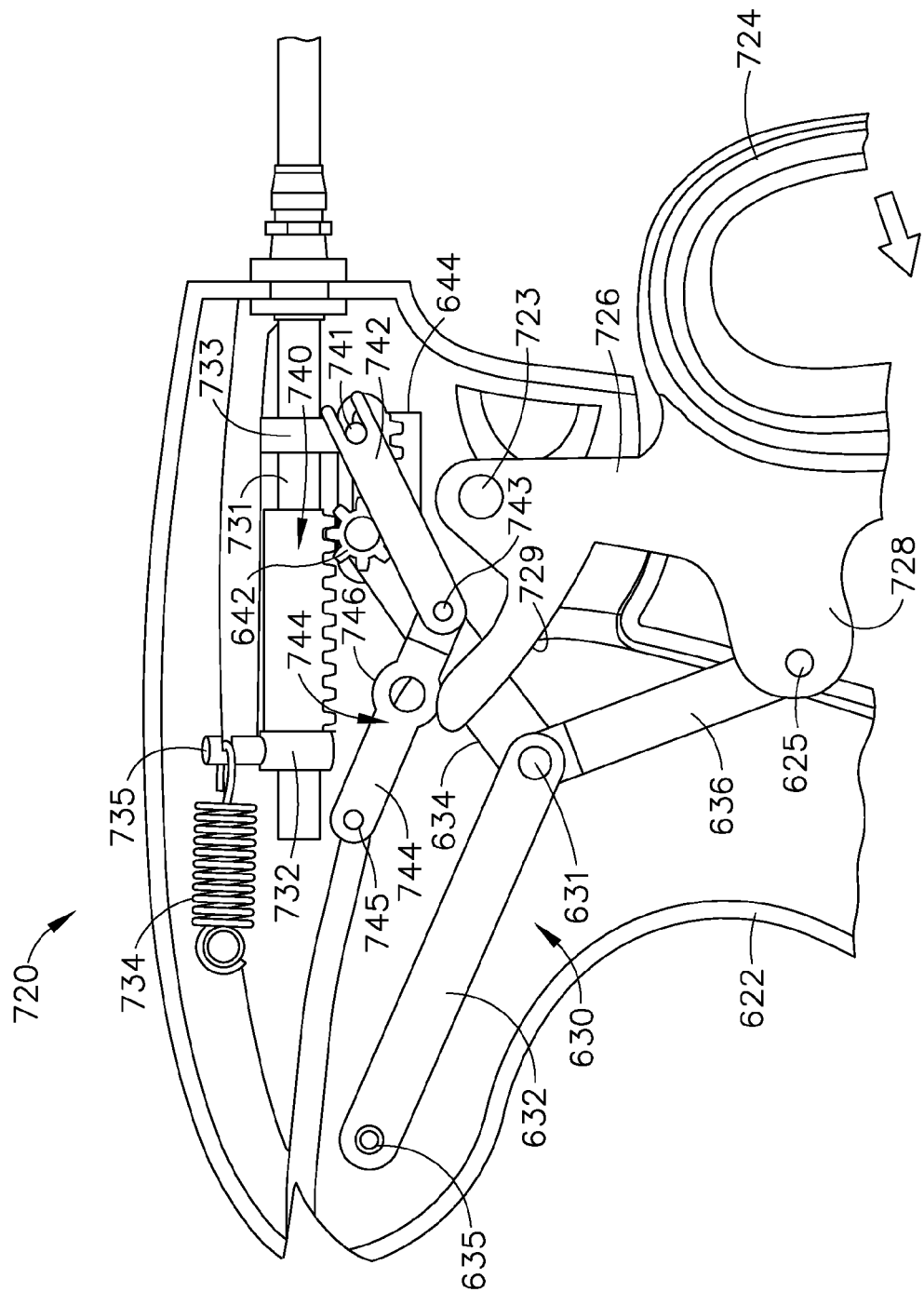
FIG. 11B depicts the handpiece of FIG. 11A, in a fired position.

In some instances, firing beam (60) may slide relative to rack (640) to close jaws (42, 44) of end effector (40) before rack (640) is translated. FIGS. 11A-11B show an exemplary handpiece (720) with a sliding rack (740). Handpiece (720) is similar to handpiece (620), except that handpiece (720) comprises sliding rack (740) and linkage assembly (730). Trigger (724) is similar to trigger (624), except that first extension (726) of trigger (724) comprises a protrusion (729) extending from first extension (726). Protrusion (729) is configured to engage linkage assembly (730). Linkage assembly (730) comprises a first linkage (744) and a second linkage (742). First linkage (744) is coupled to handpiece (720) via pin (745) such that first linkage (744) is pivotable relative to handpiece (720). First linkage (744) comprises a central protrusion (746) configured to engage protrusion (729) of trigger (724). The opposing end of first linkage (744) is coupled with second linkage (742) via pin (743). The opposing end of second linkage (742) is coupled with a sliding member (731) via pin (741). Sliding member (731) comprises a proximal flange (732) and a distal flange (733). Second linkage (742) is coupled with distal flange (733). Sliding rack (740) is similar to rack (640) and is positioned around sliding member (731) between flanges (732, 733) such that rack (740) is translatable relative to sliding member (731) between flanges (732, 733). Sliding member (731) is fixed around firing beam (60).

Trigger (724) is pivoted relative to grip (622) to actuate firing beam (60). FIG. 11A shows trigger (724) in an initial position. In this initial position, trigger (724) is positioned away from grip (622) such that gear (642) and rack (740) are in a proximal position. Sliding member (731) is also in a proximal position such that distal flange (733) contacts sliding member (731). Accordingly, firing beam (60), coupled with sliding member (731), is also in a proximal position such that jaws (42, 44) of end effector (40) are open. Jaws (42, 44) are then closed by squeezing trigger (724) toward pistol grip (722), as shown in FIG. 11B. Trigger (724) rotates within handpiece (720) via pin (723). Protrusion (729) of trigger (724) engages protrusion (746) of first linkage (744) to pivot first linkage (744) towards second linkage (742). Second linkage (742) thereby translates sliding member (731) distally until proximal flange (732) contacts rack (740). This translates firing beam (60) distally to close jaws (42, 44). Trigger (724) may be rotated at an angle of about 10 degrees to translate sliding member (731) and firing beam (60) about 0.15 to about 0.20 inches. Of course, any other of a number of angles and distances may be provided. Any of the locking features described above may be incorporated into handpiece (720) to prevent trigger (724) from continuing to pivot further toward grip (622) to translate firing beam (60) to sever tissue between jaws (42, 44) until activation button (26) has been pressed. Activation button (26) may then be depressed such that electrode surfaces (50, 52) are activated with bipolar RF energy to thermally weld the tissue layer portions captured between jaws (42, 44). Trigger (724) may then be released without severing the tissue, or trigger (724) may continue to be advanced to sever the tissue.

Trigger (724) may be pivoted further toward grip (622) to actuate linkage assembly (630) as described above to translate gear (642) and rack (740) distally. Accordingly, rack (740) translates firing beam (60) distally. Trigger (724) may be rotated at an additional angle of about 10 to about 18 degrees to translate firing beam (60) about 0.60 inches to sever tissue. Of course, any other of a number of angles or distances may be provided. Trigger (724) may then be released to return to the initial position of FIG. 11A and rack (740) and firing beam (60) to the proximal position to open jaws (42, 44). In the present example, a resilient member (734) is coupled with a protrusion (735) of sliding member (731) to bias sliding member (731) proximally to the initial position.

4. Exemplary Gear Handpiece Assembly

Figure 12:
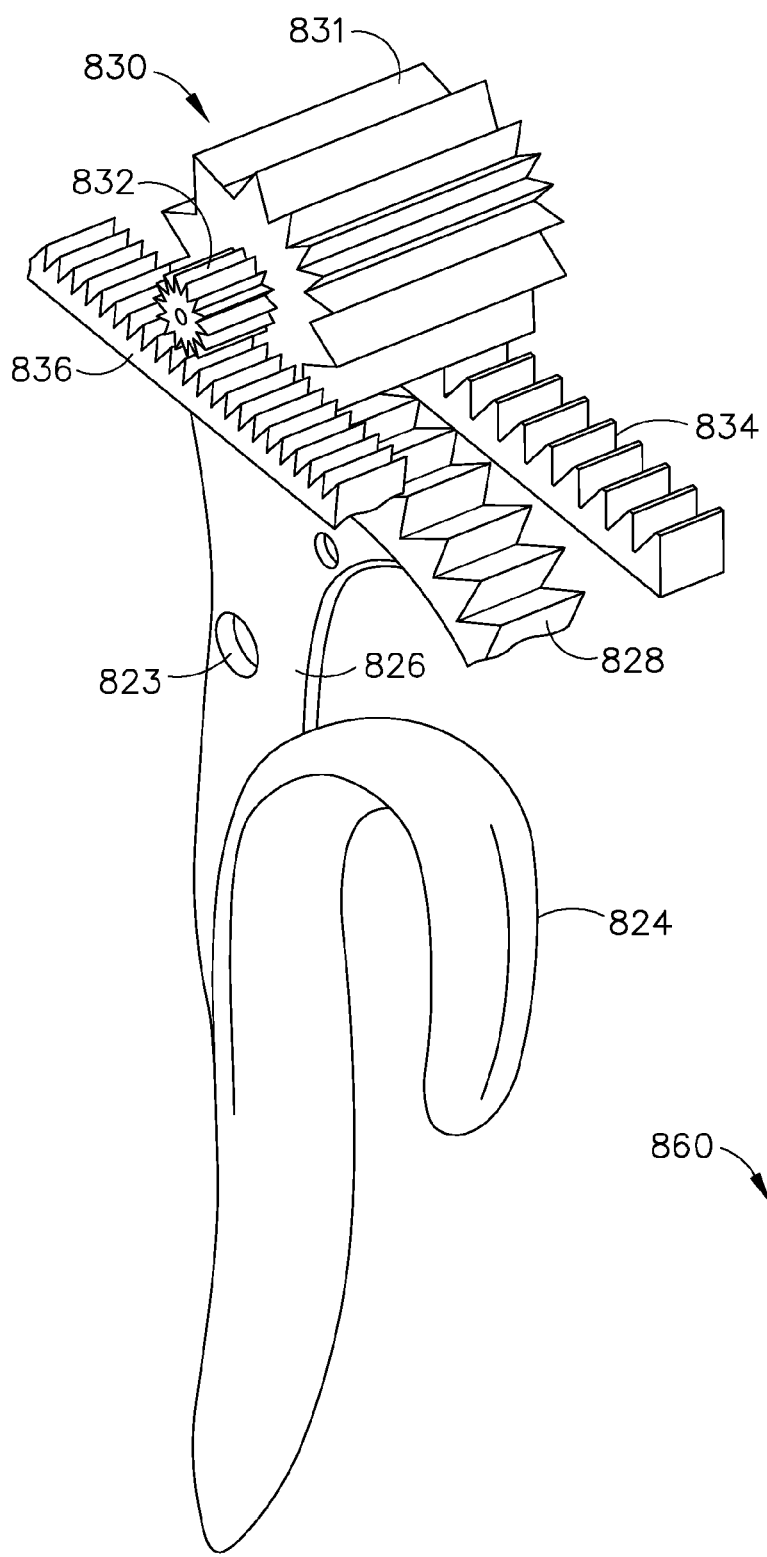
FIG. 12 depicts a partial perspective view of an exemplary trigger gear assembly.
Figure 13:
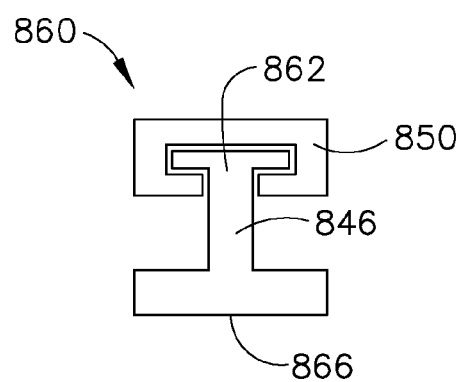
FIG. 13 depicts a cross-sectional view of an exemplary I-beam assembly for incorporation with the trigger gear assembly of FIG. 12.

FIGS. 12-14B show features of another exemplary handpiece (820) that is similar to handpiece (20), except that handpiece (820) comprises a gear assembly (830). As shown in FIG. 12, gear assembly (830) comprises a first gear (831) and a second gear (832). First and second gears (831, 832) are positioned lateral to shaft (30) within handpiece (820). First gear (831) has a larger outer diameter than second gear (832) and is coupled to a side portion of second gear (832) such that first gear (831) and second gear (832) rotate unitarily. The teeth of second gear (832) engage a second rack (836). The teeth of first gear (831) engage a first rack (834). Accordingly, first rack (834) translates at a faster rate than second rack (836) when gears (831, 832) are rotated together. The teeth of first gear (831) also engage rack teeth (828) positioned on a top portion of arm (826) of trigger (824). Teeth (828) of trigger (824) have a curved profile such that teeth (828) engage and rotate first gear (831) as trigger (824) is pivoted toward grip (822). First and second racks (834, 836) are coupled with firing beam assembly (860), shown in FIG. 13. Firing beam assembly (860) is similar to firing beam (60), except that firing beam assembly (860) comprises a clamping member (850) positioned around upper flange (862). Clamping member (850) is translatable relative to upper flange (862) to close jaw (44) toward jaw (42). The proximal end of clamping member (850) is coupled with second rack (836) and the proximal end of blade (846) is coupled with first rack (834).

Figure 14A:
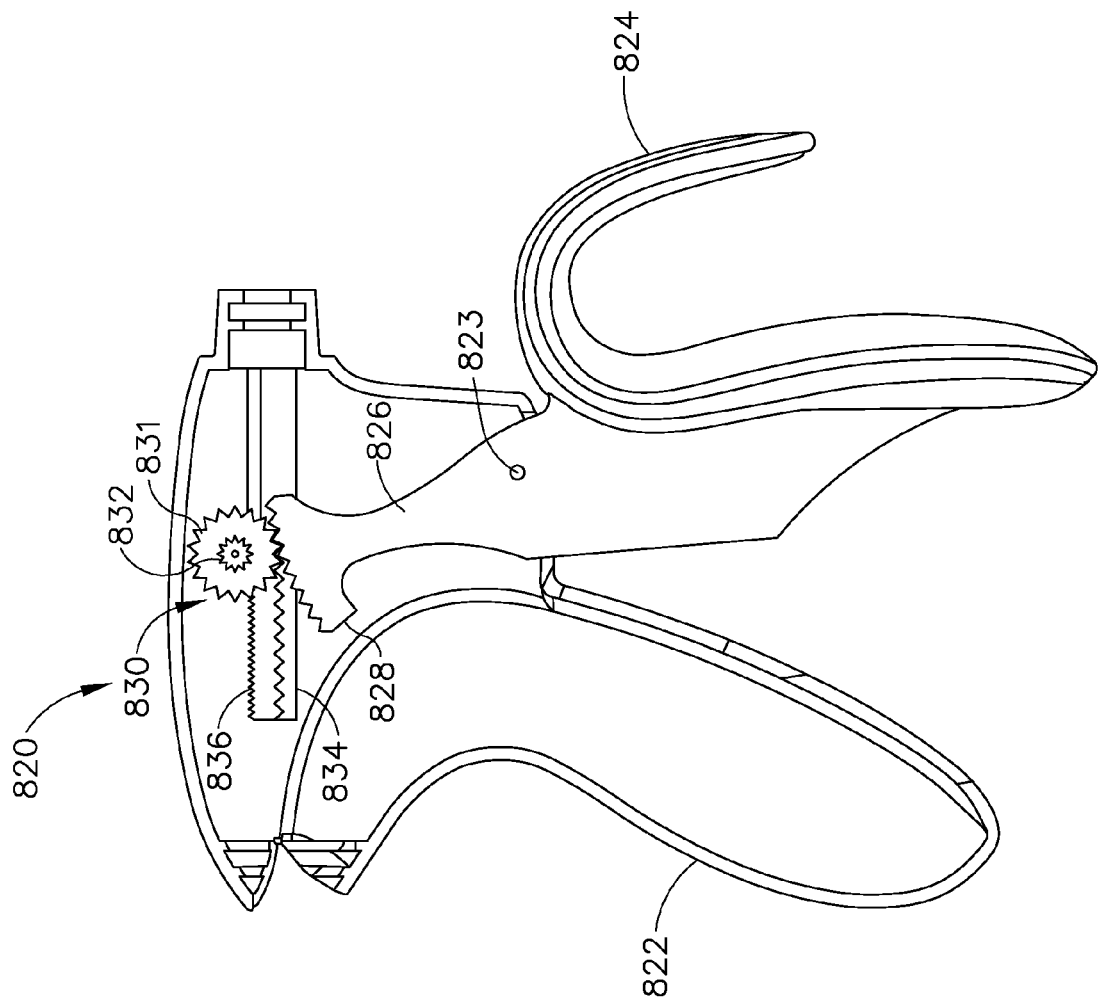
FIG. 14A depicts a partial cross-sectional view of another exemplary handpiece for incorporation in the instrument of FIG. 1, with the trigger gear assembly of FIG. 12 in an initial position.
Figure 14B:
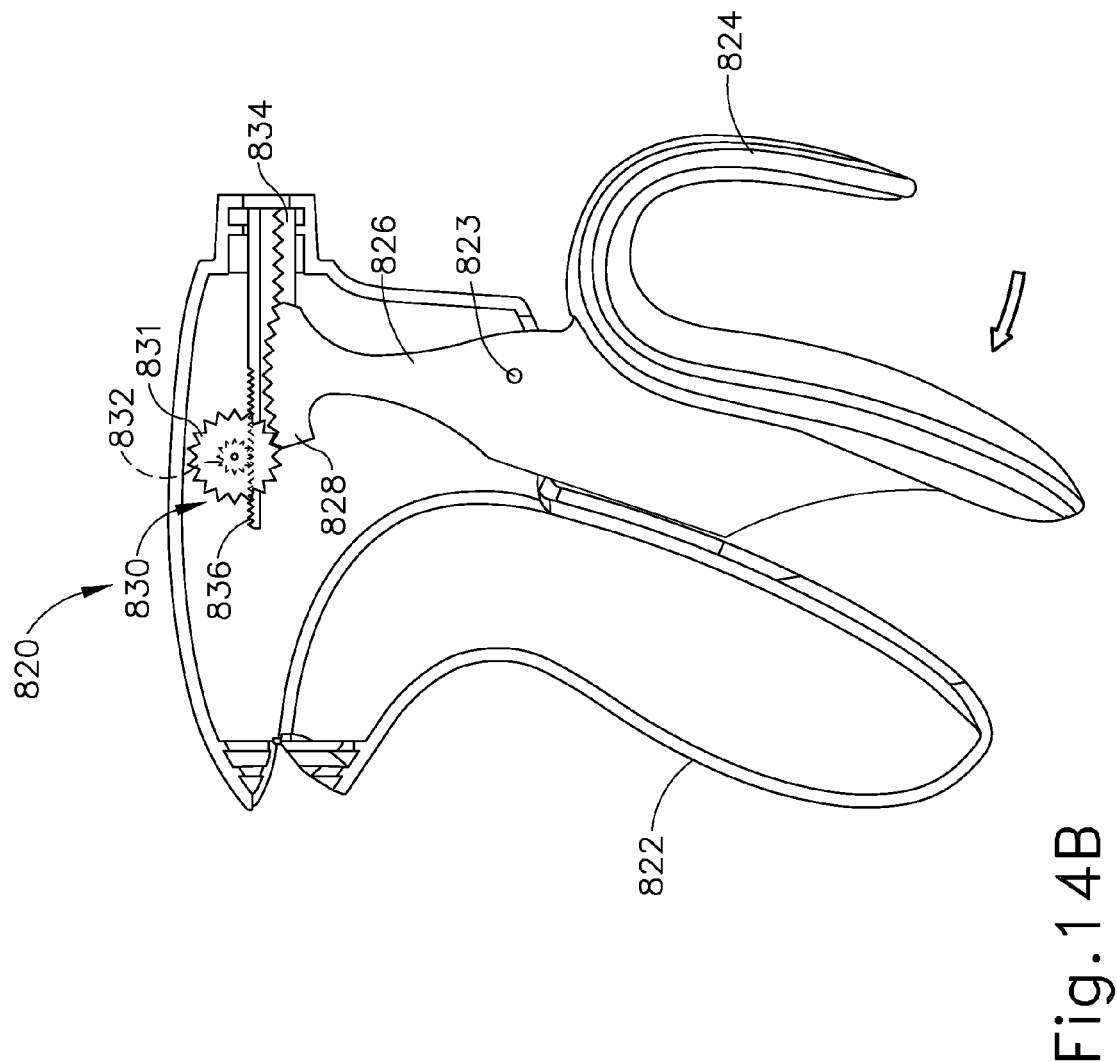
FIG. 14B depicts the handpiece of FIG. 14A, in a fired position.
Figure 15A:
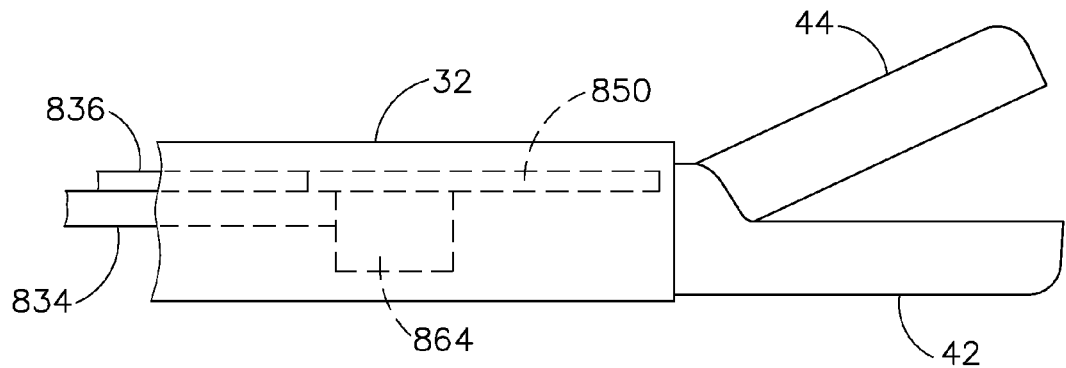
FIG. 15A depicts a cross-sectional view of an exemplary end effector for incorporation with the handpiece of FIG. 14A, in an open position.
Figure 15B:
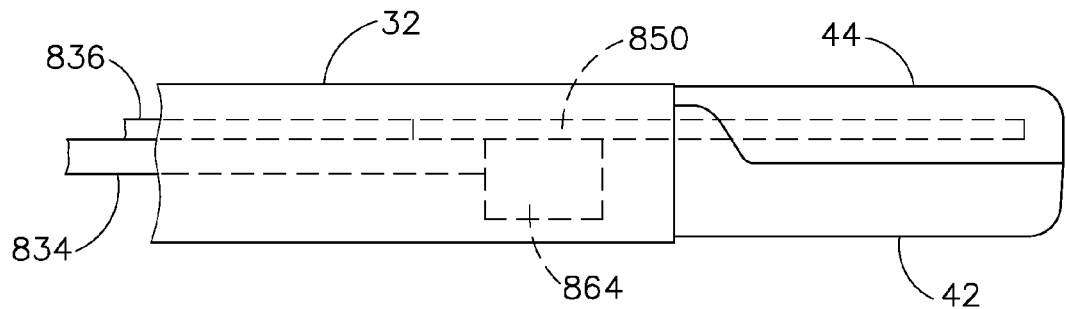
FIG. 15B depicts a cross-sectional view of the end effector of FIG. 15A in a closed and non-fired position.

Trigger (824) is pivoted relative to grip (822) to actuate firing beam assembly (860). FIG. 14A shows trigger (824) in an initial position. In this initial position, trigger (824) is positioned away from grip (822) such that the distal portion of teeth (828) of trigger (824) engage first gear (831). Racks (834, 836) are also in a proximal position such that clamping member (850) and blade (864) are proximal to jaws (42, 44), as shown in FIG. 15A. Blade (864) is proximal to clamping member (850). Jaws (42, 44) are then closed by squeezing trigger (824) toward pistol grip (822), as shown in FIG. 14B. Trigger (824) rotates within handpiece (820) via pin (823). As trigger (824) is rotated, teeth (828) of trigger (824) rotate first gear (831). First gear (831) thereby rotates second gear (832). First gear (831) engages first rack (834) to translate first rack (834) distally to thereby translate blade (864) distally. Second gear (832) engages second rack (836) to translate second rack (836) distally to thereby translate clamping member (850) distally. As shown in FIG. 15B, clamping member (850) translates distally to close jaw (44) relative to jaw (42). While clamping member (850) translates distally, blade (864) also translates distally. However, clamping member (850) closes jaws (42, 44) prior to blade (864) reaching jaws (42, 44), such that blade (864) does not yet sever any tissue captured between jaws (42, 44). Any of the locking features described above may be incorporated into handpiece (820) to prevent trigger (824) from continuing to pivot further toward grip (822) to translate blade (864) to sever tissue between jaws (42, 44) until activation button (26) has been pressed. Activation button (26) may be depressed such that electrode surfaces (50, 52) are activated with bipolar RF energy to thermally weld the tissue layer portions captured between jaws (42, 44). Trigger (824) may then be released without severing the tissue, or trigger (824) may continue to be advanced to sever the tissue.

Figure 15C:
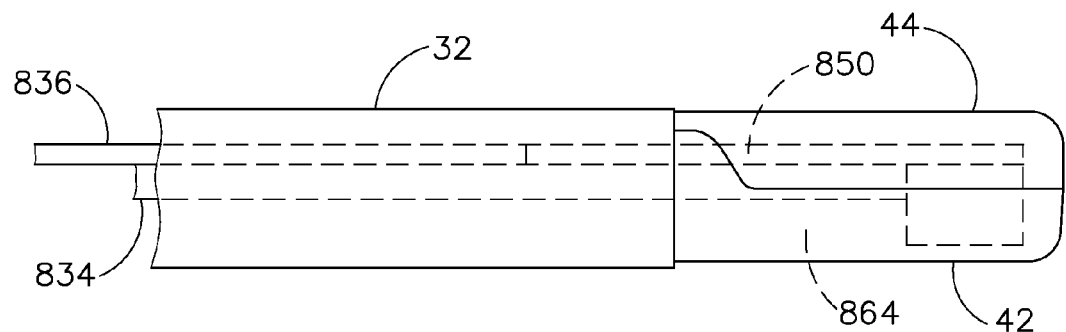
FIG. 15C depicts a cross-sectional view of the end effector of FIG. 15A in a closed and fired position.

Trigger (824) may then be pivoted further toward grip (822) to continue translating clamping member (850) and blade (864) distally, as shown in FIG. 15C. Blade (864) translates distally at a faster rate than clamping member (850). Accordingly, blade (864) translates to align with the distal portion of clamping member (850) in the present example. As blade (864) is translated distally, blade (864) severs tissue captured between jaws (42, 44). Trigger (824) may then be released to return to the initial position of FIG. 14A. Teeth (828) of trigger (824) thereby rotate gears (831, 832) in the opposing direction to translate racks (834, 836) proximally to return clamping member (850) and blade (864) to the position in FIG. 15A to open jaws (42, 44).

5. Exemplary Dual Linkage Handpiece Assembly

Figure 16A:
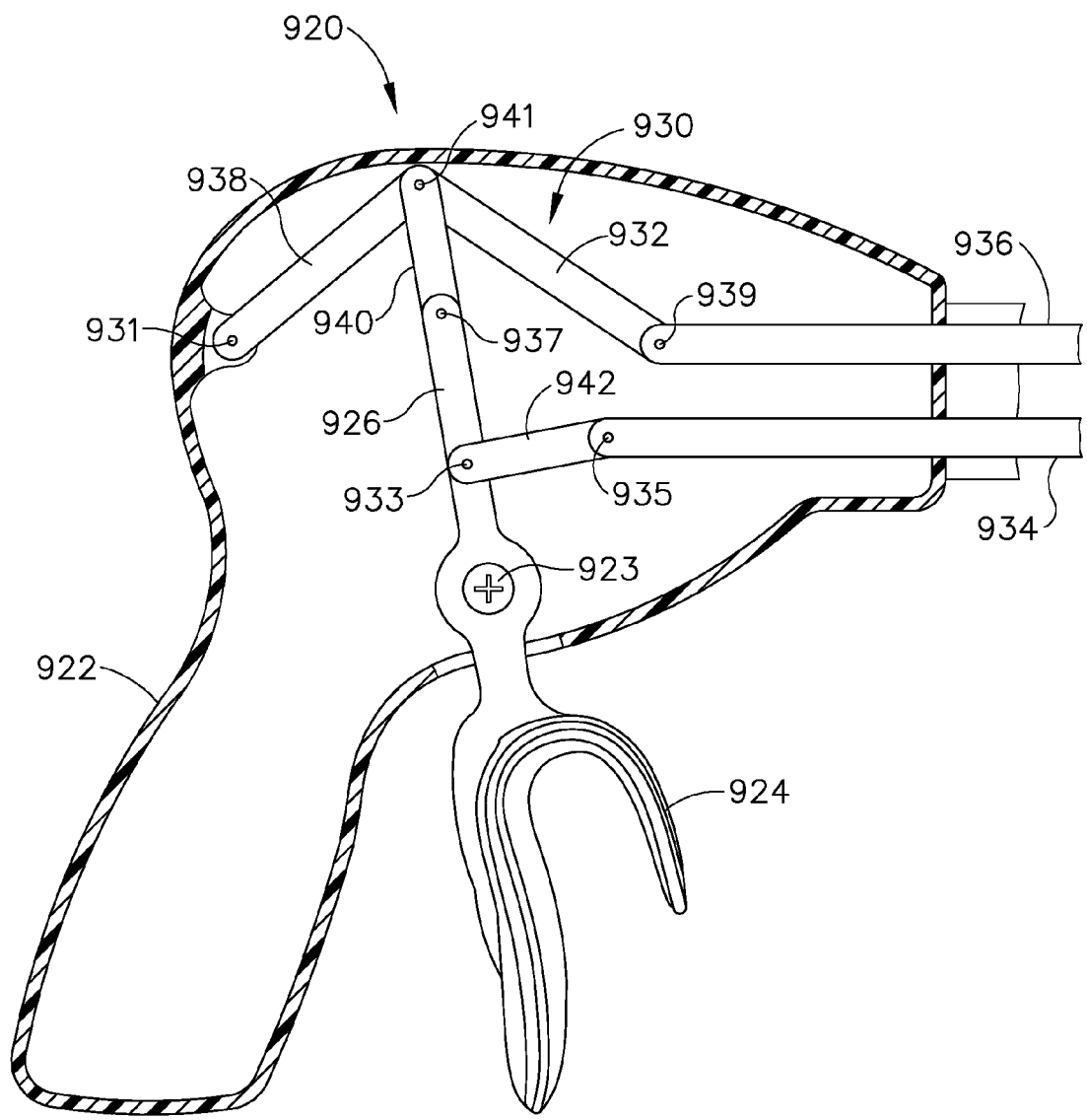
FIG. 16A depicts a partial cross-sectional view of another exemplary handpiece for incorporation in the instrument of FIG. 1, in an initial position.
Figure 16B:
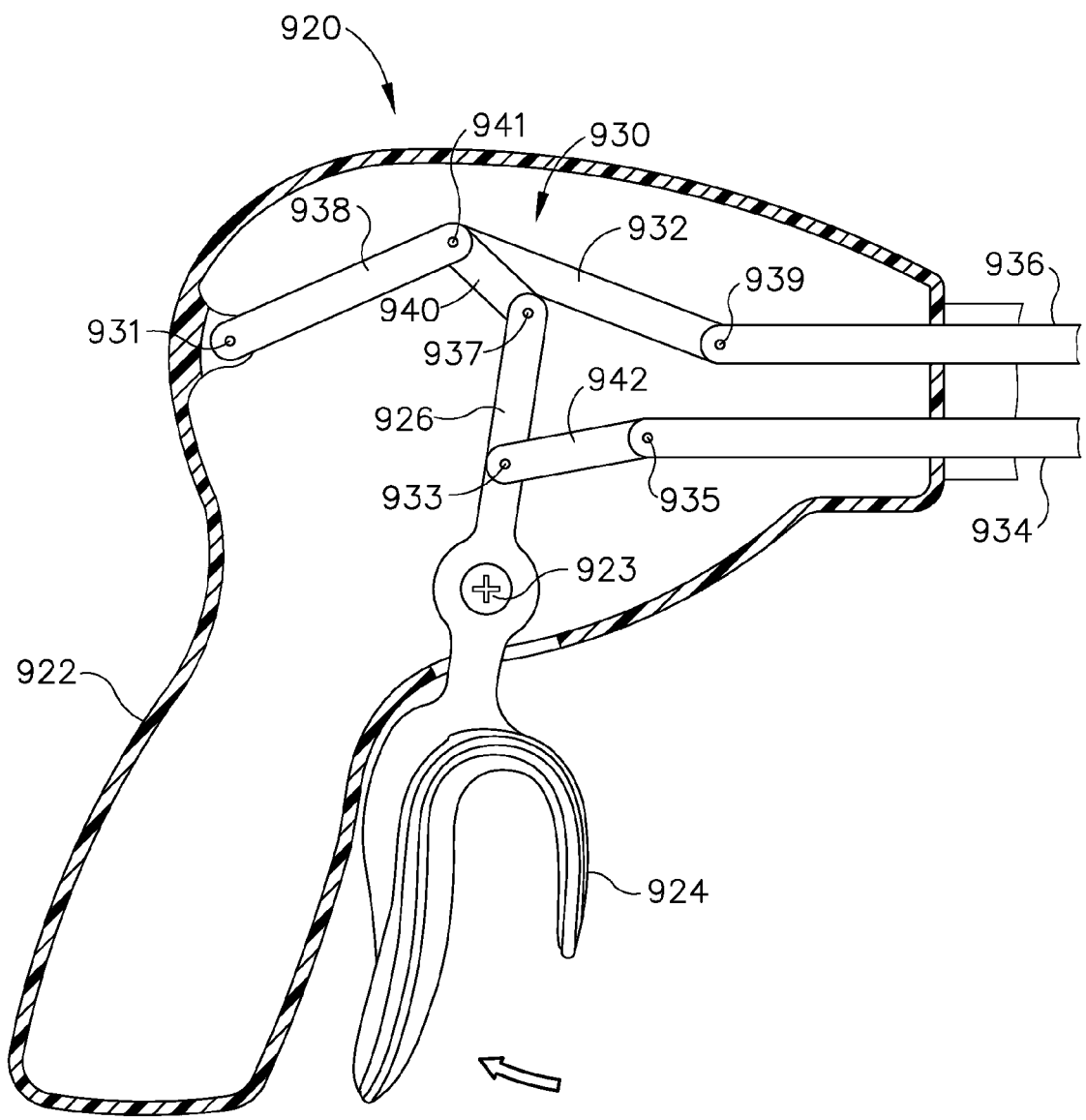
FIG. 16B depicts the handpiece of FIG. 16A, in a fired position.

FIGS. 16A-16B show another exemplary handpiece (920) that is similar to handpiece (820), except that handpiece (920) comprises a linkage assembly (930). Linkage assembly (930) comprises a first linkage (942) coupled to arm (926) of trigger (924) via pin (933). The opposing end of first linkage (942) is coupled to first translating member (934) via pin (935). The distal end of first translating member is coupled with blade (864) of firing beam assembly (860). Accordingly, trigger (824) is pivoted to pivot first linkage (942) and translate first translating member (934) and blade (864). The top portion of arm (926) of trigger (924) is coupled with a second linkage (940) via pin (937). The opposing end of second linkage (940) is coupled with a third linkage (938) and a fourth linkage (932) via pin (941). Third linkage (938) is coupled with handpiece (920) via pin (931). Fourth linkage (932) is coupled with second translating member (936) via pin (939). The distal end of second translating member (936) is coupled with clamping member (850) of firing beam assembly (860). Accordingly, trigger (924) is pivoted to pivot second linkage (940), which pivots third and fourth linkages (938, 932) to translate second translating member (936) distally to translate clamping member (850) distally. In the present example, clamping member (850) is translated at a different rate than blade (864).

Figure 17A:
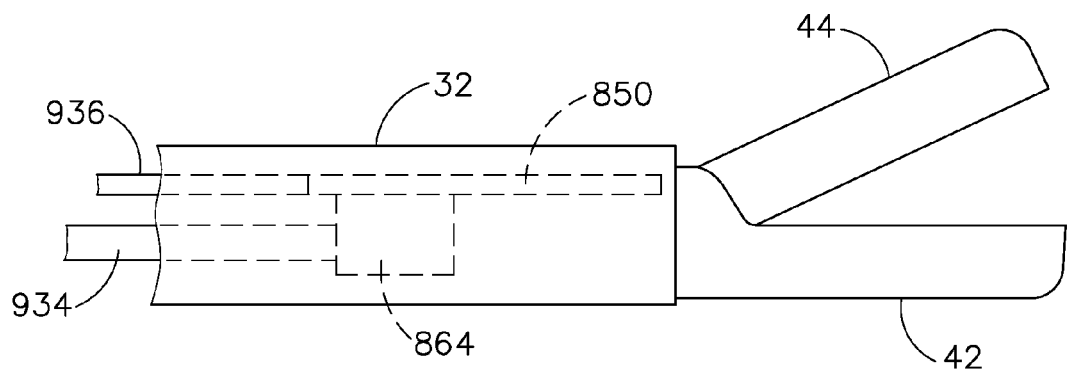
FIG. 17A depicts a cross-sectional view of an exemplary end effector for incorporation with the handpiece of FIG. 16A, in an open position.
Figure 17B:
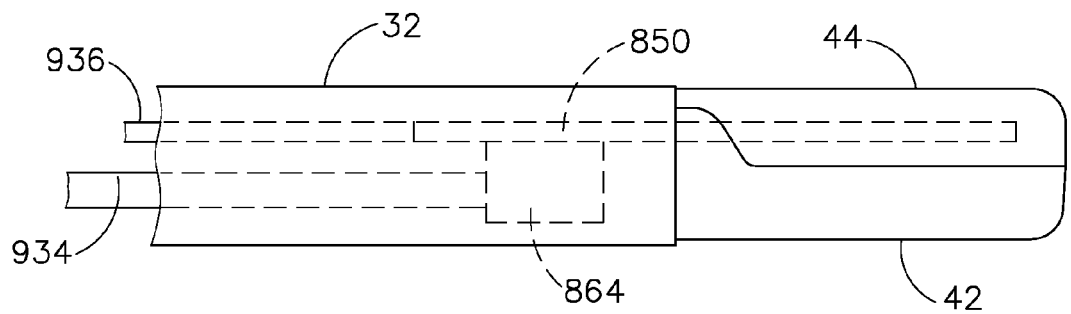
FIG. 17B depicts a cross-sectional view of the end effector of FIG. 17A in a closed and non-fired position.

Trigger (924) is pivoted relative to grip (922) to actuate firing beam assembly (860). FIG. 16A shows trigger (924) in an initial position. In this initial position, trigger (924) is positioned away from grip (922) such that linkage assembly (930) is in a first position such that clamping member (850) and blade (864) are proximal to jaws (42, 44), as shown in FIG. 17A. Jaws (42, 44) are then closed by squeezing trigger (924) toward pistol grip (922), as shown in FIG. 16B. Trigger (924) rotates within handpiece (920) via pin (923). As trigger (924) is rotated, first linkage (942) is pivoted to translate first translating member (934) distally to translate blade (864) distally. Trigger (924) also pivots second linkage (940) to pivot linkages (938, 932) to translate second translating member (936) distally to translate clamping member (850) distally. As shown in FIG. 17B, clamping member (850) translates distally to close jaw (44) relative to jaw (42). While clamping member (850) translates distally, blade (864) also translates distally. However, clamping member (850) closes jaws (42, 44) prior to blade (864) reaching jaws (42, 44), such that blade (864) does not yet sever tissue captured between jaws (42, 44). Any of the locking features described above may be incorporated into handpiece (820) to prevent trigger (924) from continuing to pivot further toward grip (922) to translate blade (864) to sever tissue between jaws (42, 44) until activation button (26) has been pressed. Activation button (26) may then be depressed such that electrode surfaces (50, 52) are activated with bipolar RF energy to thermally weld the tissue layer portions captured between jaws (42, 44). Trigger (924) may then be released without severing the tissue, or trigger (924) may continue to be advanced to sever the tissue.

Figure 17C:
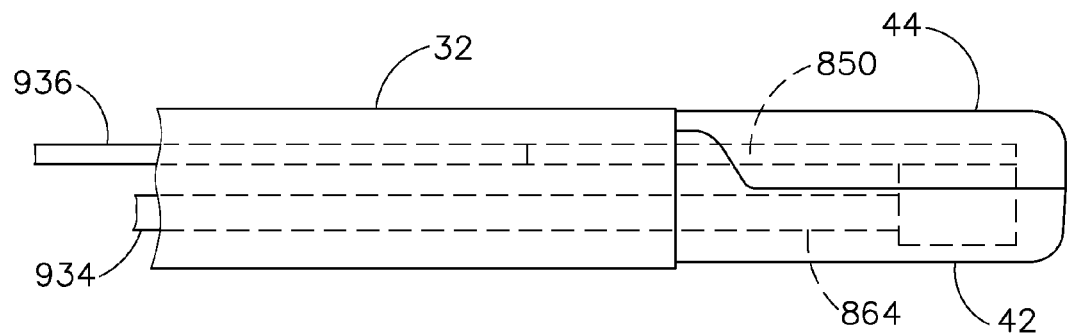
FIG. 17C depicts a cross-sectional view of the end effector of FIG. 17A in a closed and fired position.

Trigger (924) may then be pivoted further toward grip (922) to continue translating clamping member (850) and blade (864) distally, as shown in FIG. 17C. Blade (864) then translates distally to catch up to clamping member (850) in the present example. Accordingly, blade (864) translates to align with the distal portion of clamping member (850). As blade (864) is translated distally, blade (864) severs tissue captured between jaws (42, 44). Trigger (924) may then be released to return to the initial position of FIG. 16A. Linkage assembly (930) then returns to the initial position to return clamping member (850) and blade (864) to the position in FIG. 17A to open jaws (42, 44).

6. Exemplary Ratchet Handpiece Assembly

Figure 18:
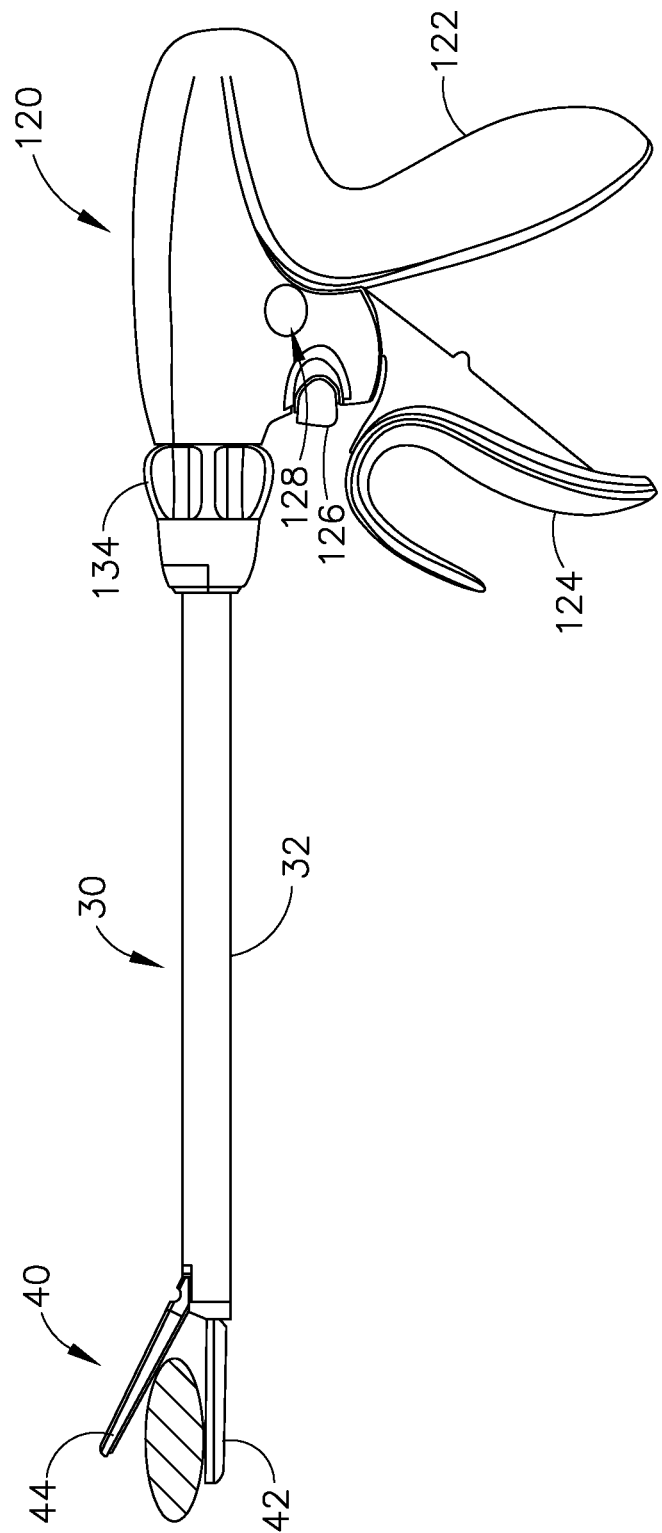
FIG. 18 depicts a side elevational view of another exemplary handpiece for incorporation in the instrument of FIG. 1.

FIG. 18 shows an exemplary handpiece (120) that is similar to handpiece (20), except that handpiece (120) comprises a ratcheting assembly (130), firing beam (140), and a stop button (128). FIGS. 19A-19D show ratcheting assembly (130) and firing beam (140) in greater detail. Firing beam (140) is similar to firing beam (60), except that firing beam (140) comprises a first longitudinal row of teeth (144) on a bottom surface of firing beam (140) and a second longitudinal row of teeth (142) on a top surface of firing beam (140). Firing beam (140) further comprises a recess (141) with a distal wall. Ratcheting assembly (130) comprises a first linkage (124), a second linkage (134), a first pawl (132), and a second pawl (146). First and second linkages (124, 134) are coupled via pin (133). First linkage (124) comprises a channel (135) extending within first linkage (124) such that pin (131) is rotatable and translatable within channel (135).

Pin (131) couples first pawl (132) with first linkage (124). First pawl (132) is configured to engage first longitudinal row of teeth (144) of firing beam (140). In some versions, first pawl (132) is resiliently biased toward the bottom side of firing beam (140) such that first pawl (132) is resiliently biased to engage teeth (144) when teeth (144) are positioned over pawl (132). Second linkage (134) is configured to engage the distal wall of recess (141) of firing beam (140). In some versions, second linkage (134) is resiliently biased toward the top side of firing beam (140) such that second linkage (134) is resiliently biased to engage recess (141) when recess (141) is positioned under the free end of linkage (134). A second pawl (146) is coupled with handpiece (120) via pin (145) and engages the second longitudinal row of teeth (142) of firing beam (140). In some versions, second pawl (146) is resiliently biased toward the top side of firing beam (140) such that second pawl (146) is resiliently biased to engage teeth (142) when teeth (142) are positioned under pawl (146). A resilient member (148) is coupled to a proximal end of firing beam (140) and a portion of handpiece (120) to bias firing beam (140) in the proximal direction.

Figure 19A:
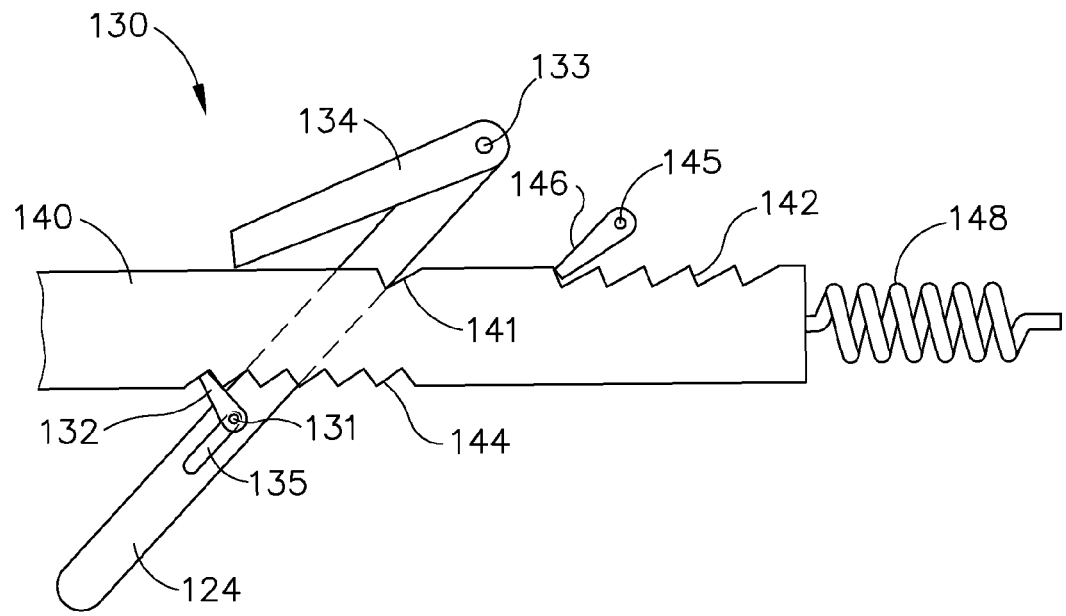
FIG. 19A depicts a partial side elevational view of a ratchet assembly of the handpiece of FIG. 18 in a first position.

Trigger (124) is pivoted relative to grip (122) to actuate firing beam (140). FIG. 19A shows ratcheting assembly (130) in an initial position. In this initial position, pawls (132, 146) engage teeth (144, 142) of firing beam (140) and second linkage (134) is disengaged from recess (141). Trigger (124) is then pivoted toward grip (122) to ratchet firing beam (140) distally. When trigger (124) is pivoted, trigger (124) pivots first linkage (124) such that first pawl (132) translates to engage the next proximal tooth in the first longitudinal row of teeth (144). Trigger (124) is then released such that pawl (132) incrementally translates firing beam (140) distally as pawl (132) engages each tooth of longitudinal row of teeth (144). Pawl (146) engages teeth (142) to longitudinally hold firing beam (140) in place while pawl (132) is repositioned on teeth (144). This allows firing beam (140) to incrementally close jaws (42, 44) (e.g., by repeatedly pivoting trigger (124) with short strokes). Activation button (126) may be pressed after each incremental movement of firing beam (140) to apply RF energy to incrementally weld the tissue layers captured between jaws (42, 44). An indication may be provided to indicate to the user when the increment of tissue has been sealed. For example, the indication may be visual, audible, tactile, etc.

Figure 19B:
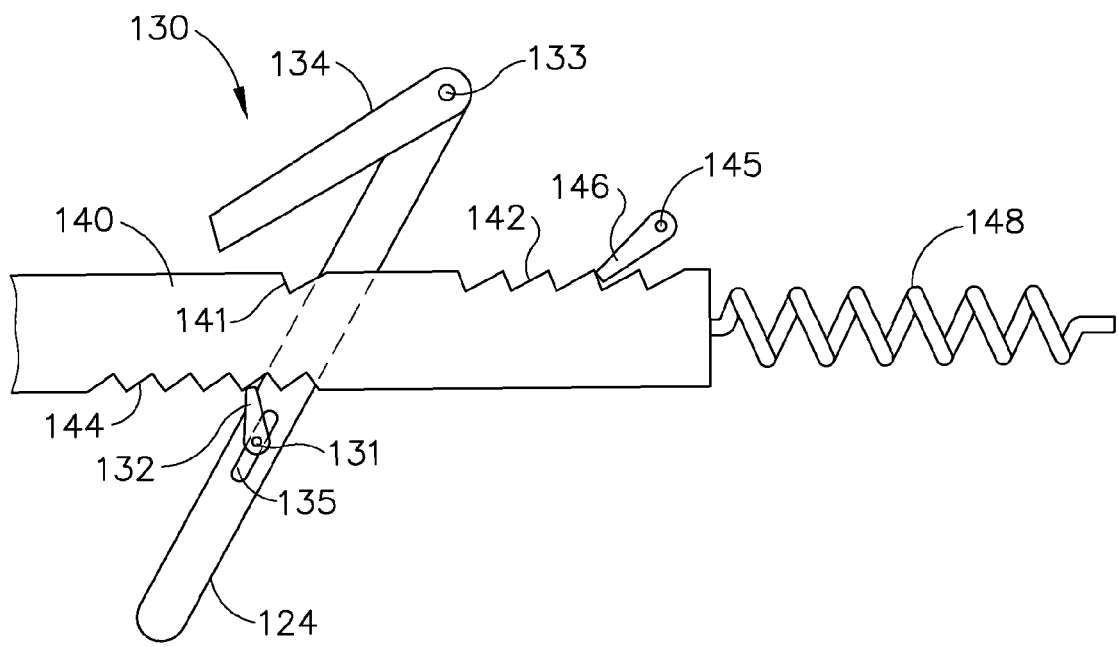
FIG. 19B depicts a partial side elevational view of the ratchet assembly of FIG. 19A in a second position.
Figure 19C:
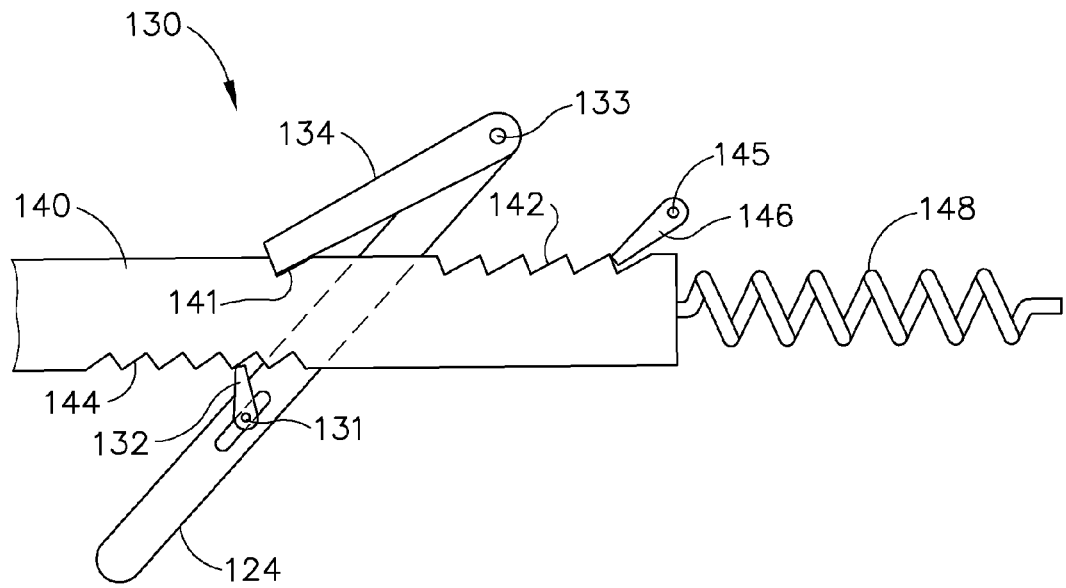
FIG. 19C depicts a partial side elevational view of the ratchet assembly of FIG. 19A in a third position.

FIG. 19B shows ratcheting assembly (130) after firing beam (140) has been translated distally several increments. Alternatively, a stop button (128) may be used instead of ratcheting assembly (130). For instance, stop button (128) may be pressed to allow trigger (124) to pivot firing beam (140) to a next increment until stop button (128) is released. In both instances, trigger (124) is pivoted until firing beam (140) is translated distally to fully close jaws (42, 44) and second linkage (134) engages recess (141) of firing beam (140), as shown in FIG. 19C. Any of the locking features described above may be incorporated into handpiece (120) to prevent trigger (124) from continuing to pivot further toward grip (122) to translate firing beam (140) to sever tissue between jaws (42, 44) until activation button (126) has been pressed. Activation button (126) may then be depressed such that electrode surfaces (50, 52) are activated with bipolar RF energy to thermally weld the tissue layer portions captured between jaws (42, 44). Trigger (124) may then be released without severing the tissue, or trigger (124) may continue to be advanced to sever the tissue.

Figure 19D:
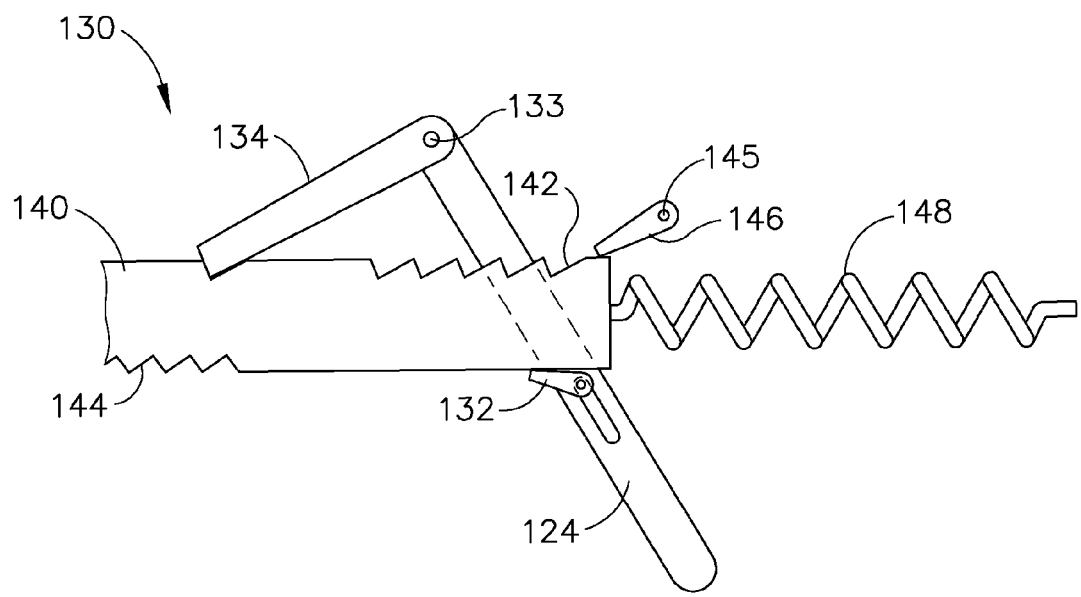
FIG. 19D depicts a partial side elevational view of the ratchet assembly of FIG. 19A in a fourth position.

Trigger (124) continues to pivot toward grip (122). As shown in FIG. 19D, trigger (124) pivots first linkage (124) to thereby pivot second linkage (134). Second linkage (134) engages recess (141) of firing beam to advance firing beam (140) distally to sever tissue captured between jaws (42, 44). In the present example, pawls (132, 146) disengage teeth (144, 142) as firing beam (140) is advanced to sever tissue. Trigger (124) may then be released such that resilient member (148) pulls firing beam (140) proximally to open jaws (42, 44). Pawls (132, 146) are held in an open position such that pawls (132, 146) fail to engage teeth (144, 142) as firing beam (140) is returned proximally.

Figure 20:
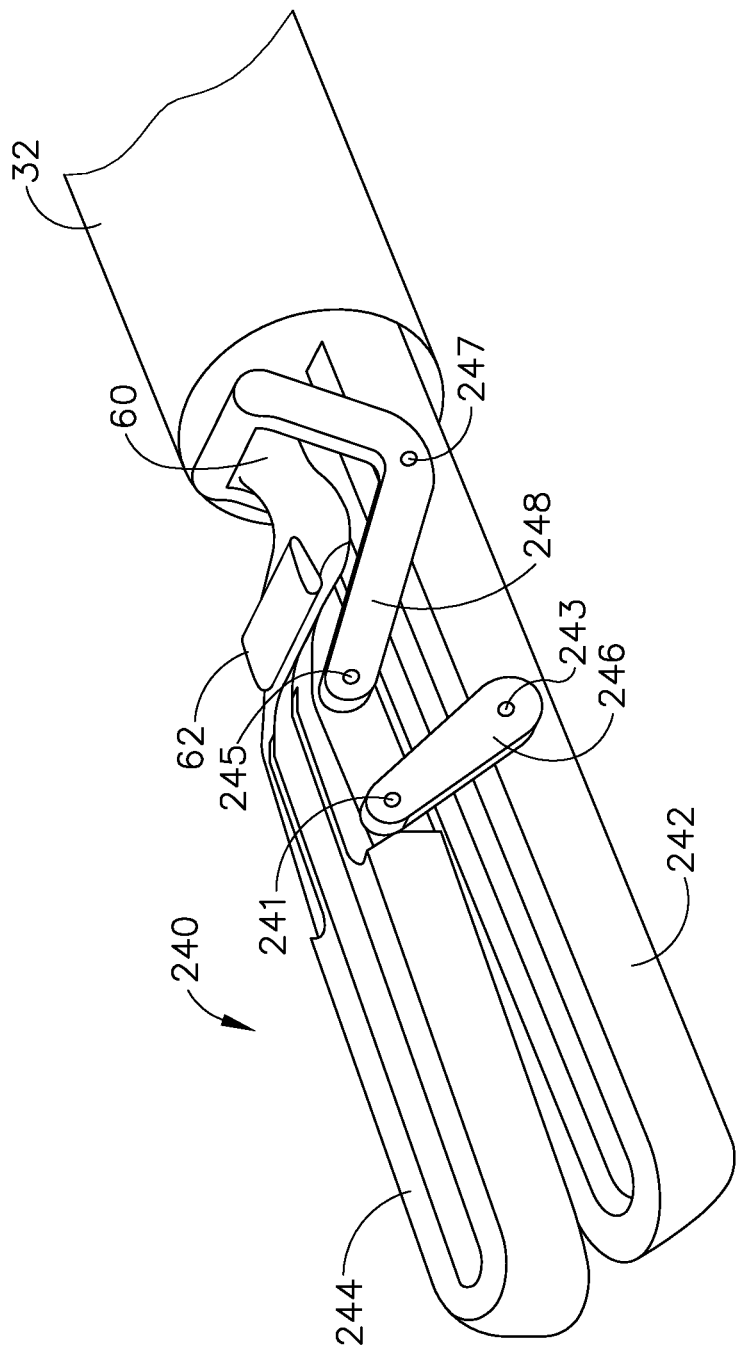
FIG. 20 depicts a perspective view of an end effector for use with the handpiece of FIG. 18.

In some instances, it may be desirable to close jaws (42, 44) in a parallel fashion when jaws (42, 44) are closed incrementally to prevent tissue from pooling out of the sides of jaws (42, 44). For example, this may be desirable when a liver is transected. FIGS. 20-21C show an exemplary alternative end effector (240). End effector (240) is similar to end effector (40), except that end effector (240) comprises linkages (246, 248) on each side of end effector (240). First linkage (246) is coupled with jaw (244) via pin (241) and is coupled with jaw (242) via pin (243). Second linkage (248) is coupled with jaw (244) via pin (245) and is coupled with jaw (242) via pin (247). Second linkage (248) is proximal to first linkage (246). Linkages (246, 248) pivot relative to jaws (242, 244) to allow jaws (242, 244) to close in a parallel fashion.

Figure 21A:
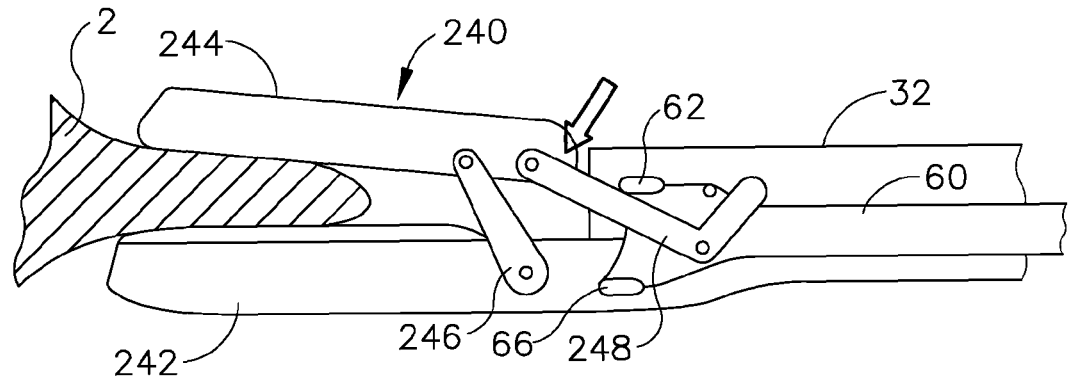
FIG. 21A depicts a cross-sectional view of the end effector of FIG. 20 in a first position.
Figure 21B:
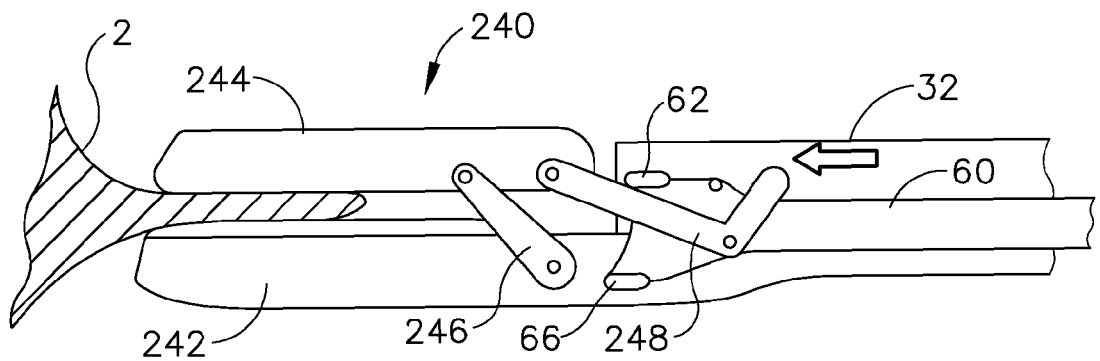
FIG. 21B depicts a cross-sectional view of the end effector of FIG. 20 in a second position.
Figure 21C:
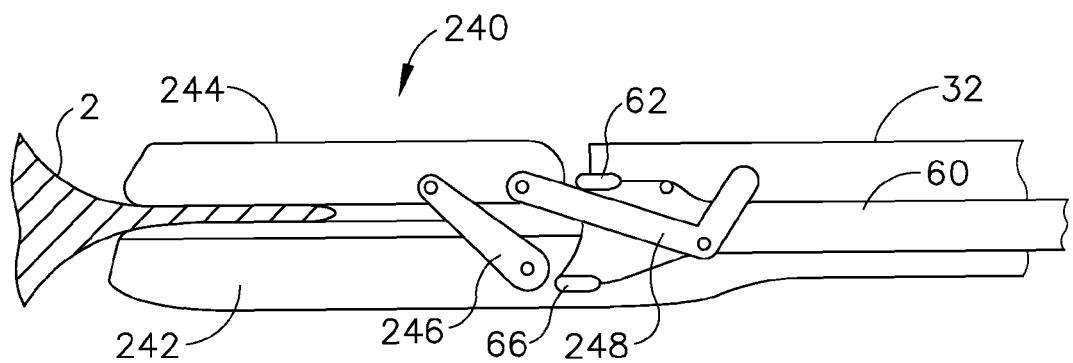
FIG. 21C depicts a cross-sectional view of the end effector of FIG. 20 in a third position.

FIGS. 21A-21C show jaws (242, 244) as firing beam (60) is advanced to close jaws (242, 244). As shown in FIG. 21A, jaws (242, 244) are positioned around a tissue portion (2). Linkages (246, 248) allow jaws (242, 244) to open wider around tissue (2) than they would otherwise be allowed to open if they were coupled at a single pivot. Firing beam (60) is then advanced distally, as shown in FIG. 21B. As firing beam (60) is advanced, upper flange (62) engages linkage (248) to cammingly pivot linkage (248). Linkage (248) thereby closes jaw (244) relative to jaw (242). As jaw (244) closes, linkage (246) also pivots to maintain jaw (244) substantially parallel to jaw (242) as jaws (242, 244) compress tissue (2). As shown in FIG. 21C, firing beam (60) is continued to advance distally to cammingly pivot linkages (248, 246) and complete the closure of jaws (244) toward jaw along a path that is perpendicular to the tissue contacting surfaces of jaws (242, 244).

B. Exemplary End Effector Assemblies

End effector (40) may also be modified to fully close jaws (42, 44) of end effector (40) prior to severing tissue captured between jaws (42, 44). FIGS. 22-24C show another exemplary end effector (1040) with such closing features. As best seen in FIG. 22, end effector (1040) comprises jaws (1042, 1044) and a closure tube (1033). Jaw (1042) is similar to jaw (42) and jaw (1044) is similar to jaw (44), except that jaw (1044) comprises camming surfaces (1046). Jaws (1042, 1044) are pivotally coupled by a pin (1047). Closure tube (1033) is slidably disposed about an outer sheath (not shown) that is similar to outer sheath (32) described above. Closure tube (1033) is operable to bear against camming surfaces (1046) to drive jaw (1044) toward jaw (1042). Closure tube (1033) includes a transverse opening (1035) that is configured to pivotably receive a coupling pin (1070) as will be described in greater detail below.

End effector (1040) of the present example further comprises a firing beam (1050). Firing beam (1050) of this example is substantially similar to firing beam (60) described above in that firing beam (1050) includes flanges (1062, 1066) and a distal blade (64). However, firing beam (1050) of this example also includes a longitudinally extending slot (1052), which is configured to receive coupling pin (1070). Slot (1052) includes a distal portion (1054) that has a greater height than the rest of slot (1052). Distal portion (1052) includes a flat edge (1056).

Coupling pin (1070) has a D-shaped profile and is disposed in opening (1035) and slot (1052) as noted above. Coupling pin (1070) includes a flat surface (1072) and a stem (1074). Coupling pin (1070) and closure tube (1033) are coupled such that coupling pin (1070) and closure tube (1033) do not translate relative to one another. Instead, they translate together. However, coupling pin (1070) is rotatable within opening (1035) of closure tube (1033). Coupling pin (1070) and firing beam (1050) are coupled such that coupling pin (1070) and firing beam (1050) will translate together when coupling pin (1070) is disposed in distal portion (1052) of slot (1052), with flat edge (1056) contacting flat surface (1072). However, when flat edge (1056) is no longer in contact with flat surface (1072), firing beam (1050) may translate relative to coupling pin (1070). The driving engagement between coupling pin (1070) and firing beam (1050) is determined based on the angular orientation of coupling pin (1070) as will be described in greater detail below. The angular orientation of coupling pin (1070) is controlled by engagement between stem (1074) and a fixed boss (1080) in end effector (1040).

Figure 24A:
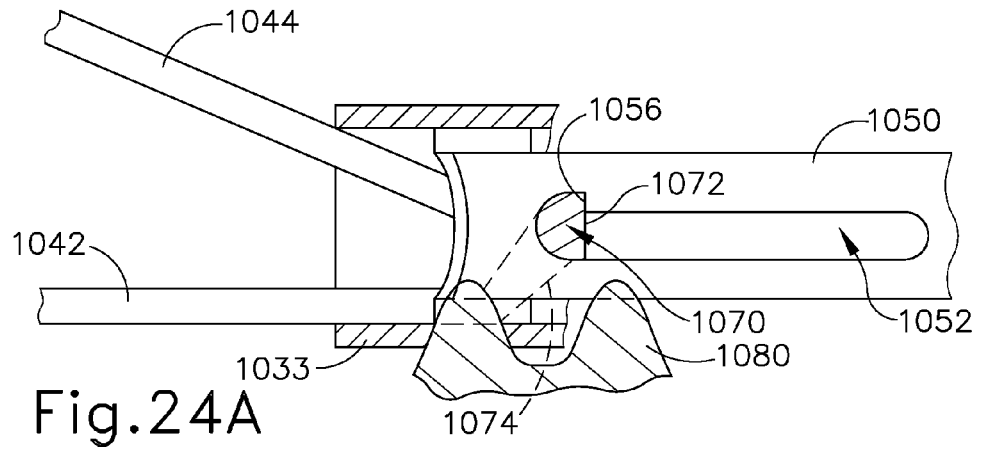
FIG. 24A depicts a cross-sectional view of the firing beam, closure tube, and coupling pin of FIG. 23 in a first position.
Figure 24B:
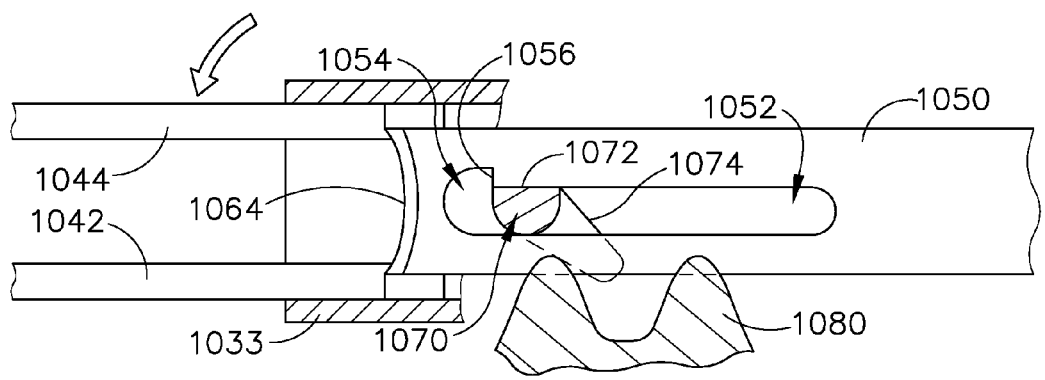
FIG. 24B depicts a cross-sectional view of the firing beam, closure tube, and coupling pin of FIG. 23 in a second position.
Figure 24C:
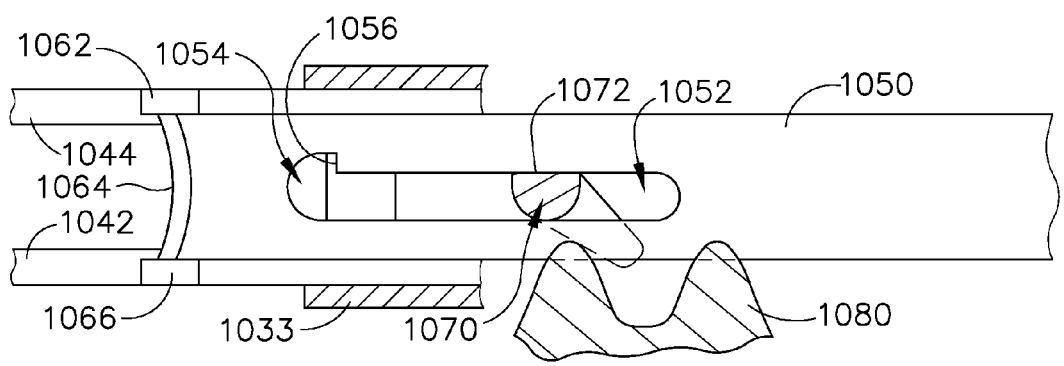
FIG. 24C depicts a cross-sectional view of the firing beam, closure tube, and coupling pin of FIG. 23 in a third position.

FIGS. 24A-24C show different stages of firing beam (1050) advancement, showing staged interactions between firing beam (1050) and closure tube (1033). In FIG. 24A, firing beam (1050) and closure tube (1033) are coupled together by coupling pin (1070). Coupling pin (1070) is angularly oriented such that flat edge (1056) of slot (1052) in firing beam (1050) is in contact with flat surface (1072) of coupling pin (1070). Jaw (1044) is open at this stage, and firing beam (1050) is in a proximal position. As firing beam (1050) is advanced distally to the position shown in FIG. 24B, firing beam (1050) initially drives closure tube (1033) distally. In particular, flat edge (1056) bears distally on flat surface (1072), such that coupling pin (1070) transfers the distal driving force to closure tube (1033). The distal end of closure tube (1033) bears against camming surfaces (1046) of upper jaw (1044) during this range of travel, thereby closing upper jaw (1044) toward lower jaw (1042) to clamp tissue between jaws (1042, 1044). Distal blade (1064) has not yet severed any tissue between jaws (1042, 1044) at this stage.

After reaching the point where closure tube (1033) has closed jaws (1042, 1044), stem (1074) engages fixed boss (1080) in end effector (1040). As firing beam (1050) continues to advance distally, engagement between stem (1074) and fixed boss (1080) rotates coupling pin (1070) such that the angular orientation of coupling pin (1070) changes by approximately 90 degrees. With coupling pin (1070) reoriented, flat edge (1056) no longer contacts flat surface (1072) of coupling pin (1070). Thus, as firing beam (1050) continues to advance distally with coupling pin (1070) reoriented, firing beam (1050) no longer bears against coupling pin (1070). Instead, coupling pin (1070) stays stationary while firing beam (1050) travels distally. This relative movement is provided by the configuration of slot (1052), which enables longitudinal movement of firing beam (1050) relative to coupling pin (1070). It should be understood that, since coupling pin (1070) is stationary during this range of distal travel by firing beam (1050), closure tube (1033) is also stationary during this range of distal travel by firing beam (1050), as shown in FIG. 24C. Firing beam (1050) severs tissue captured between jaws (1042, 1044) during this range of travel.

After firing beam (1050) has completed a full distal stroke, firing beam (1050) may be retracted proximally. Again, coupling pin (1070) and closure tube (1033) remain stationary during a first range of proximal travel by firing beam (1050). However, firing beam (1050) eventually reaches a point where coupling pin (1070) contacts the distal end of slot (1052). Once this occurs and firing beam (1050) continues to retract proximally, firing beam (1050) drives coupling pin (1070) and closure tube (1030) proximally. During this range of proximal travel, stem (1074) again contacts fixed boss (1080), and this engagement rotates coupling pin (1070) once again such that coupling pin (1070) is returned to the angular orientation shown in FIG. 24A. Thus, the above-described process may be repeated as many times as desired. It should be understood that upper jaw (1044) may be driven open by a camming feature within end effector (1040), by a resilient feature within end effector (1040), and/or in some other suitable fashion as closure tube (1033) is retracted proximally during the final proximal range of travel of firing beam (1050).

Figure 25:
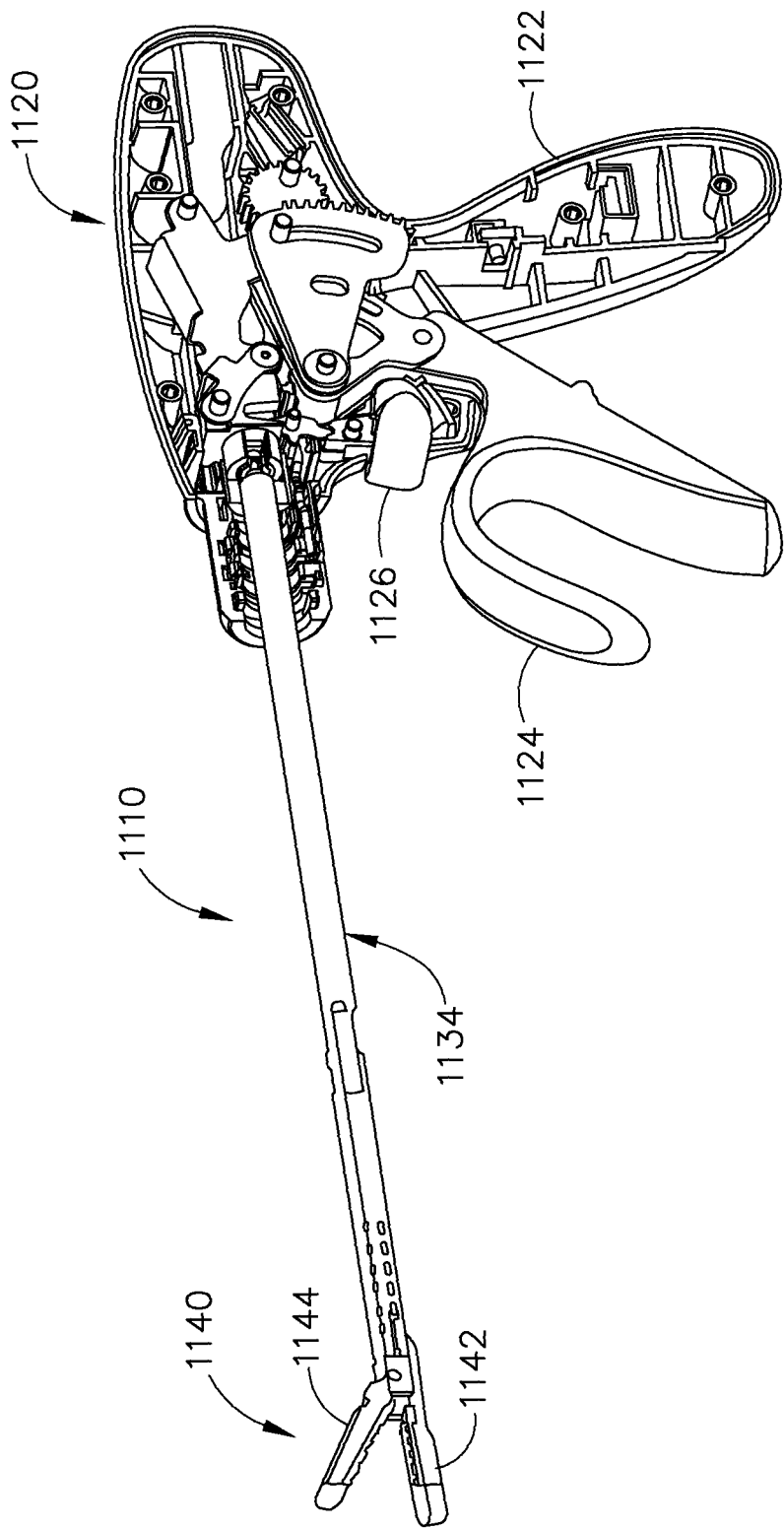
FIG. 25 depicts a cross-sectional view of another exemplary electrosurgical medical instrument.
Figure 26:
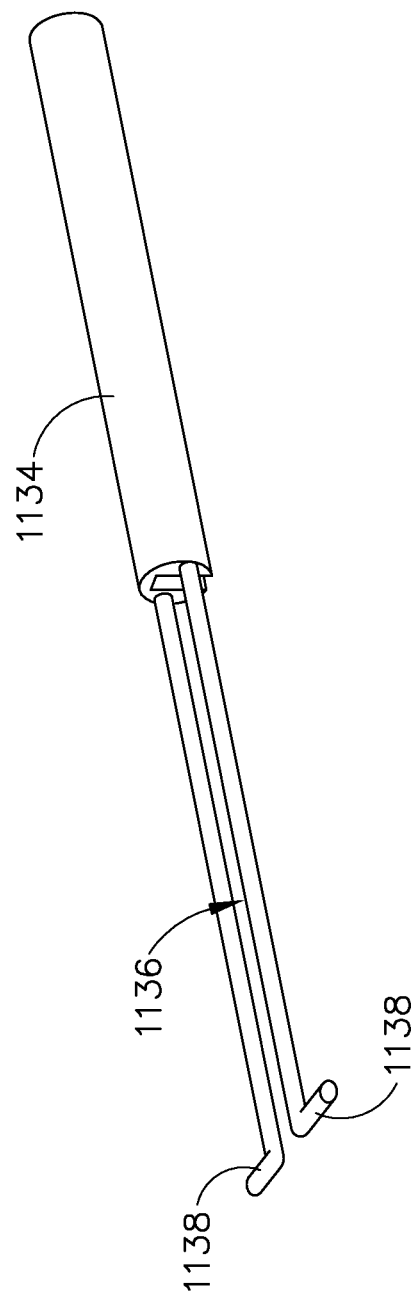
FIG. 26 depicts a perspective view of a cam tube of the instrument of FIG. 25.
Figure 27:
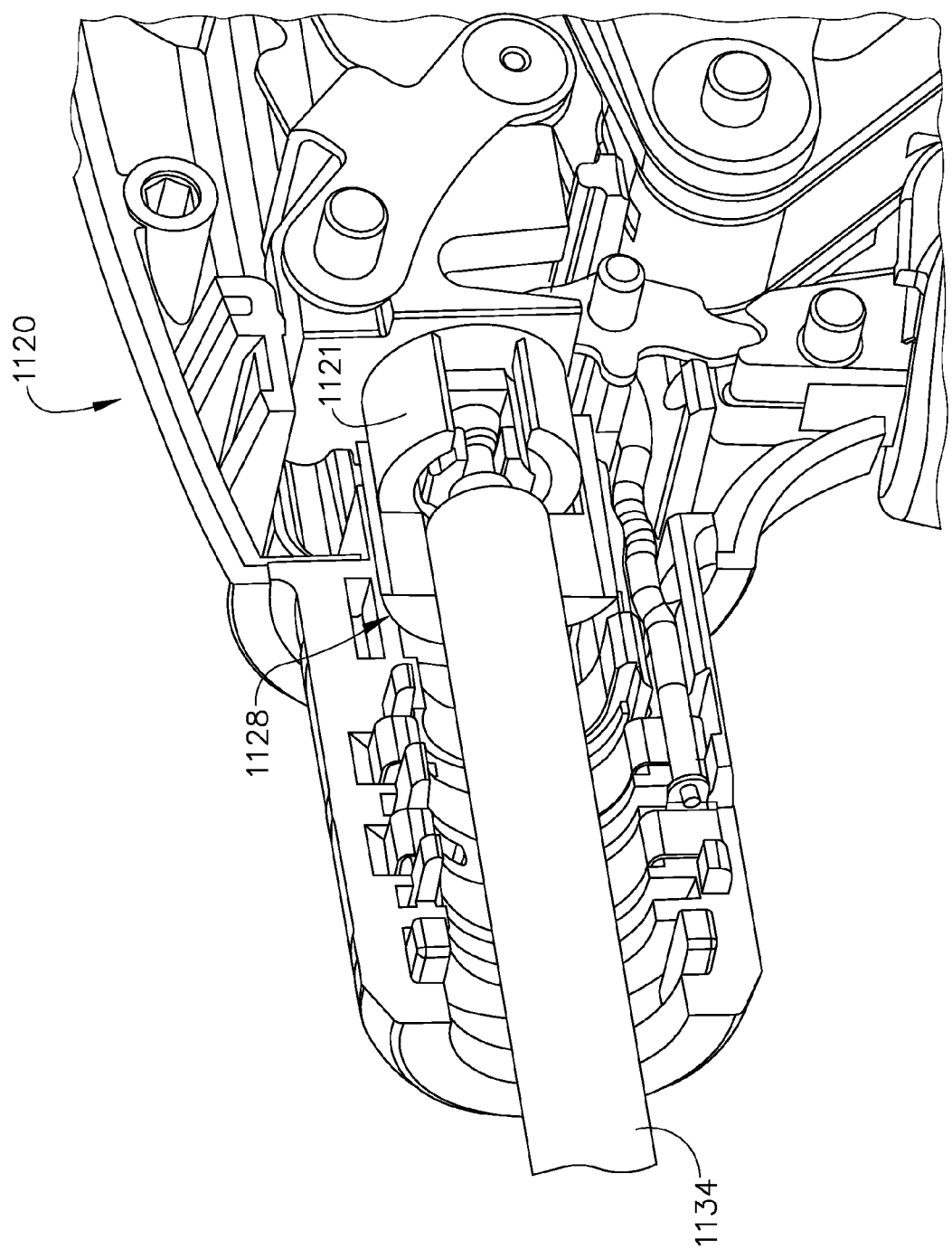
FIG. 27 depicts a cross-sectional view of a handpiece of the instrument of FIG. 25.

FIGS. 25-28B show another exemplary end effector (1140) with camming surfaces (1146). FIG. 25 shows instrument (1110) with end effector (1140). Instrument (1110) is similar to instrument (10), except that instrument (1110) comprises a camming outer shaft (1134), as shown in FIG. 26. Shaft (1134) is slidably disposed in an outer sheath (not shown) that is similar to outer sheath (32) described above. Shaft (1134) comprises a recess (1136) and pins (1138). Recess (1136) extends within shaft (1134) from the distal end of shaft (1134) to accommodate firing beam (60). Pins (1138) extend outwardly from each side of the distal end of shaft (1134). Pins (1138) are configured to engage camming surfaces (1146) of end effector (1140). As shown in FIG. 27, the proximal end of shaft (1134) is coupled with handpiece (1120). Handpiece (1120) is similar to handpiece (20) except that handpiece (1120) comprises a shaft coupling feature (1128). Shaft coupling feature (1128) is positioned around the proximal end of shaft (1134) to couple shaft (1134) with yoke (1121). Yoke (1121) is coupled with trigger (1124). Accordingly, when trigger (1124) is pivoted toward grip (1122), yoke (1121) translates distally to thereby translate coupling feature (1128) and shaft (1134) distally.

Figure 28A:
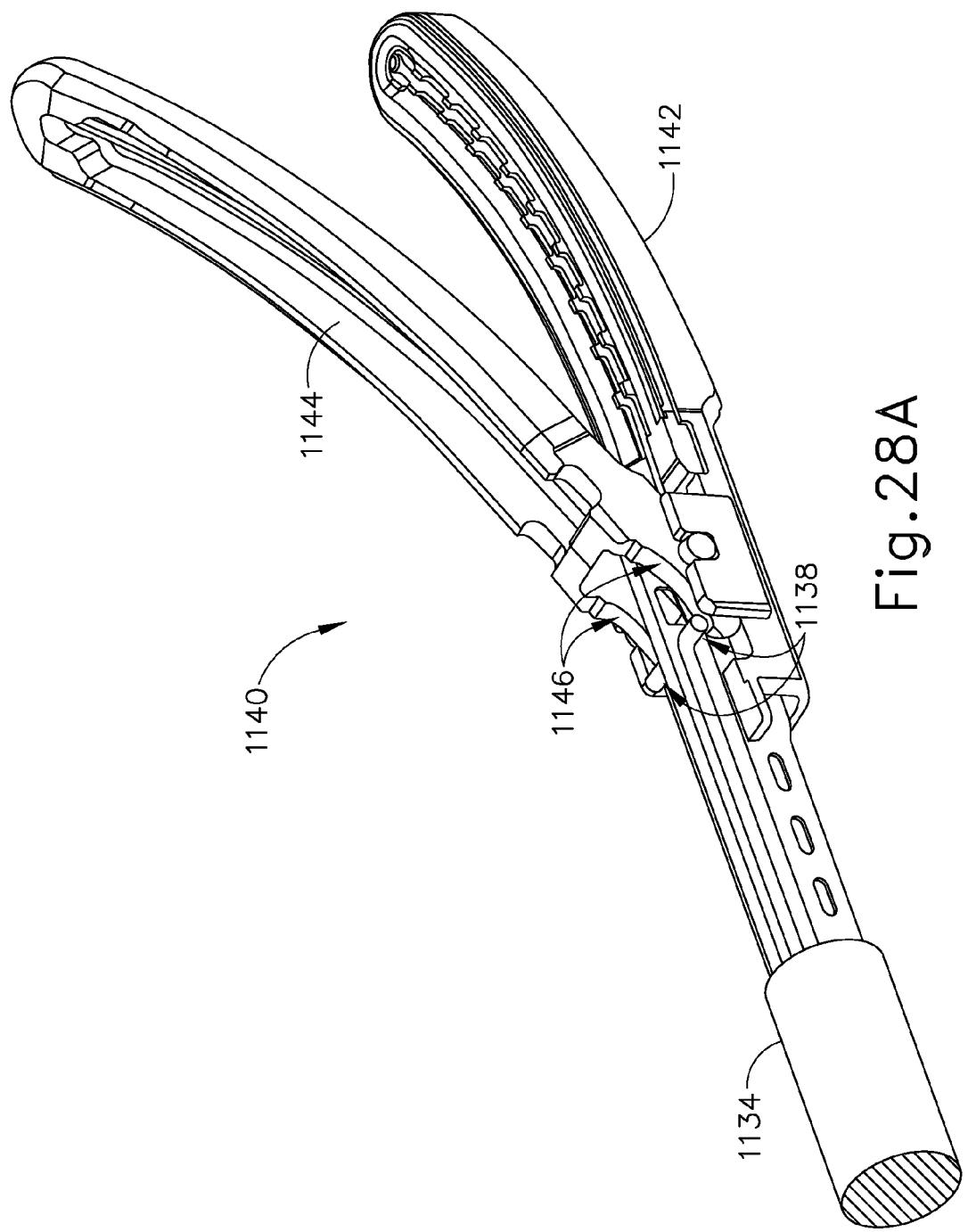
FIG. 28A depicts a partial perspective view of an end effector of the instrument of FIG. 25 in an open position.
Figure 28B:
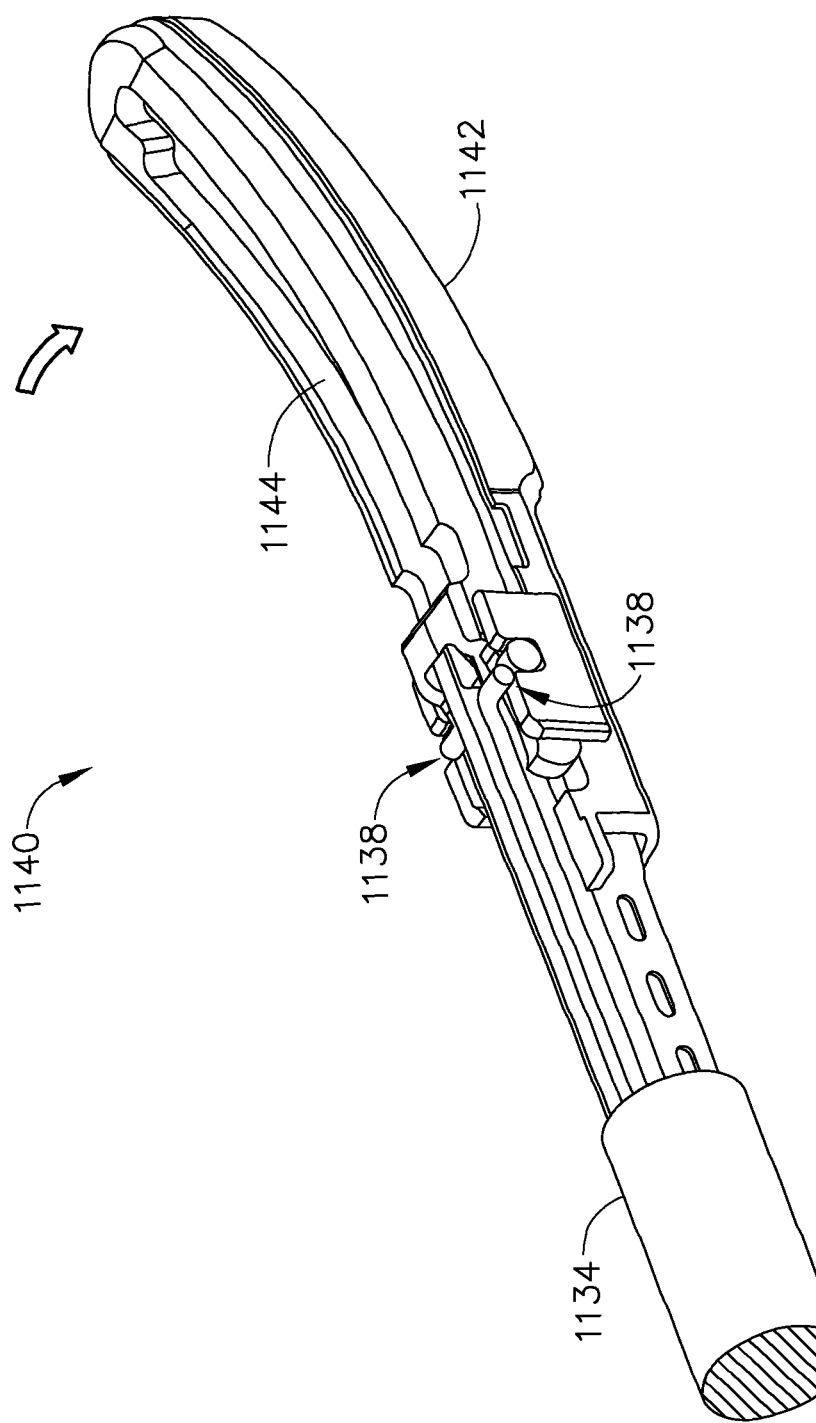
FIG. 28B depicts a partial perspective view of the end effector of FIG. 28A in a closed position.

The distal end of shaft (1134) is coupled with end effector (1140), as shown in FIG. 28A. End effector (1140) is similar to end effector (40), except that end effector (1140) comprises camming surfaces (1146) on the proximal end of jaw (1144). Camming surfaces (1146) are configured to receive pins (1138) of shaft (1134) such that pins (1138) slide distally along camming surfaces (1146) to close jaws (1142, 1144). FIG. 28A shows end effector (1140) in an open position. In the present example, pins (1138) of shaft (1134) are proximal to jaw (1144). Shaft (1134) is then translated distally to close jaws (1142, 1144), as shown in FIG. 28B. When shaft (1134) is translated distally, pins (1138) of shaft (1134) slide distally along camming surfaces (1146) of jaw (1144) to camming pivot jaw (1144) toward jaw (1142). This occurs before firing beam (60) severs tissue between jaws (1142, 1144). Any of the locking features described above may be incorporated into handpiece (1120) to prevent trigger (1124) from continuing to pivot further toward grip (1122) to translate firing beam (60) to sever tissue between jaws (1142, 1144) until activation button (1126) has been pressed. Activation button (1126) may be depressed such that electrode surfaces (50, 52) are activated with bipolar RF energy to thermally weld the tissue layer portions captured between jaws (1142, 1144). Trigger (1124) may then be released without severing the tissue, or trigger (1124) may continue to be advanced to sever the tissue. If trigger (1124) if pivoted further toward grip (1122), firing beam (60) advances through recess (1136) of shaft (1134) to sever tissue captured between jaws (1142, 1144). Trigger (1124) may then be released to pull firing beam (60) and shaft (1134) proximally. Pins (1138) then slide proximally along camming surfaces (1146) of jaw (1144) and allow jaw (1144) to pivot away from jaw (1142) to open jaws (1142, 1144), as shown in FIG. 28A. In some versions, camming surfaces (1146) are configured such that pins (1138) drive jaw (1144) open when shaft (1134) is refracted proximally.

III. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379 (issued as U.S. Pat. No. 9,161,803 on Oct. 27, 2015), entitled "Motor Driven Electrosurgical Device with Mechanical and Electrical Feedback," published May 10, 2012, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

In versions where the teachings herein are applied to a surgical stapling instrument, it should be understood that the teachings herein may be combined with the teachings of one or more of the following, the disclosures of all of which are incorporated by reference herein: U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193 (issued as U.S. Pat. No. 8,408,439 on Apr. 2, 2013), entitled "Surgical Stapling Instrument with An Articulatable End Effector," published Oct. 21, 2010; and U.S. Pub. No. 2012/0239012 (issued as U.S. Pat. No. 8,453,914 on Jun. 4, 2013), entitled "Motor-Driven Surgical Cutting Instrument with Electric Actuator Directional Control Assembly," published Sep. 20, 2012. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006 (abandoned), the disclosure of which is incorporated by reference herein; U.S. Pat. Pub. No. 2007/0191713, entitled "Ultrasonic Device for Cutting and Coagulating," published Aug. 16, 2007 (abandoned), the disclosure of which is incorporated by reference herein; U.S. Pat. Pub. No. 2007/0282333, entitled "Ultrasonic Waveguide and Blade," published Dec. 6, 2007 (abandoned), the disclosure of which is incorporated by reference herein; U.S. Pat. Pub. No. 2008/0200940, entitled "Ultrasonic Device for Cutting and Coagulating," published Aug. 21, 2008 (abandoned), the disclosure of which is incorporated by reference herein; U.S. Pat. Pub. No. 2011/0015660 (issued as U.S. Pat. No. 8,461,744 on Jun. 11, 2013), entitled "Rotating Transducer Mount for Ultrasonic Surgical Instruments," published Jan. 20, 2011, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011 (issued as U.S. Pat. No. 8,939,974 on Apr. 14, 2011, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An instrument comprising:
   (a) a first jaw;
   (b) a second jaw movable relative to the first jaw from an open position to a closed position, wherein the second jaw is operable to capture tissue between the first and second jaw in the closed position, wherein the end effector is operable to apply bipolar RF energy to tissue captured between the first and second jaws;
   (c) a firing beam, wherein the firing beam comprises a sharp distal end, wherein the firing beam is translatable between the first and second jaws among longitudinal positions comprising:
      (i) a proximal position where the second jaw is in the open position,
      (ii) a first distal position where the second jaw is in the closed position, wherein the end effector is operable to apply bipolar RF energy when the firing beam is in the first distal position, and
      (iii) a second distal position where the sharp distal end of the firing beam is operable to sever tissue captured between the first and second jaws; and
   (d) a lockout feature, wherein the lockout feature is operable to allow the firing beam to travel from the proximal position to the first distal position, wherein the lockout feature is operable to prevent the firing beam from advancing from the first distal position to the second distal position until the lockout feature is actuated.

2. The instrument of claim 1 further comprising a handpiece coupled with the end effector, wherein the handpiece comprises a first actuator operable to translate the firing beam of the end effector.

3. The instrument of claim 2, wherein the handpiece comprises a sliding linkage assembly, wherein the sliding linkage assembly comprises a first linkage slidable within a channel of the handpiece, wherein the first actuator is coupled with the first linkage to slide the first linkage within the channel, wherein the sliding linkage assembly is operable to translate the firing beam.

4. The instrument of claim 2, wherein the first actuator comprises a first cam and a second cam, wherein the first cam is operable translate the firing beam from the proximal position to the first distal position, wherein the second cam is operable to translate the firing beam from the first distal position to the second distal position.

5. The instrument of claim 2, wherein the handpiece comprises a rack assembly, wherein the rack assembly comprises a first rack secured to the handpiece, a second rack secured to the firing beam, and a gear coupled with the first actuator, wherein the gear is positioned between the first rack and the second rack such that the first actuator is operable to rotate the gear to translate the gear relative to the first and second racks to thereby translate the firing beam.

6. The instrument of claim 5, wherein the rack assembly further comprises a translating member, wherein the translating member comprises a proximal flange and a distal flange, wherein the translating member is positioned around the firing beam, wherein the second rack is positioned around the translating member such that the second rack is translatable relative to the translating member.

7. The instrument of claim 2, wherein the handpiece comprises a ratchet assembly, wherein the ratchet assembly is operable to incrementally close the second jaw relative to the first jaw.

8. The instrument of claim 7, wherein the end effector is operable to apply bipolar RF energy between each increment that the second jaw is closed.

9. The instrument of claim 2, further comprising a clamping member positioned around a portion of the firing beam, wherein the clamping member is translatable relative to the firing beam, wherein the clamping member is operable to close the second jaw.

10. The instrument of claim 9, wherein the handpiece further comprises a gear assembly, wherein the gear assembly comprises a first gear and a second gear, wherein the first gear is coupled with the clamping member, wherein the second gear is coupled with the firing beam, wherein the first actuator is operable to actuate the gear assembly to thereby translate the clamping member and the firing beam.

11. The instrument of claim 9, wherein the handpiece comprises a linkage assembly, wherein the linkage assembly comprises a first linkage coupled with the clamping and a second linkage coupled with the firing beam, wherein the first actuator is operable to actuate the linkage assembly to thereby translate the clamping member and the firing beam.

12. The instrument of claim 2, wherein the handpiece comprises a second actuator operable to activate the bipolar RF energy to the end effector.

13. The instrument of claim 12, wherein the lockout feature is coupled with the second actuator.

14. The instrument of claim 13, wherein the lockout feature comprises a rib positioned on the first actuator and a channel positioned within the second actuator, wherein the rib is offset with the channel until the second actuator is actuated.

15. The instrument of claim 13, wherein the lockout feature comprises a linkage assembly, wherein the linkage assembly is configured to engage the firing beam until the second actuator is actuated.

16. The instrument of claim 13, wherein the lockout feature comprises a resilient member, wherein the resilient member is configured to bias the lockout feature to engage the firing beam.

17. The instrument of claim 2, wherein the first actuator is configured to rotate about 10 degrees to translate the firing beam from the proximal position to the first distal position.

18. The instrument of claim 2, wherein the first actuator is configured to rotate about 28 degrees to translate the firing beam from the proximal position to the second distal position.

19. An apparatus comprising:
(a) a driver assembly comprising:
  (i) a body, and
  (ii) an actuator movably coupled to the body;
(b) a shaft extending distally from the body;
(c) an end effector located at a distal end of the shaft, wherein the end effector comprises:
  (i) a first jaw, and
  (ii) a second jaw movable relative to the first jaw to capture tissue between the first jaw and the second jaw;
(d) a firing beam comprising a proximal end and a sharp distal end, wherein the firing beam is translatable relative to the shaft, wherein the proximal end of the firing beam coupled with the actuator; and
(e) a closure tube comprising a proximal end and a distal end, wherein the closure tube is translatable relative to the shaft and the firing beam, wherein the proximal end of the closure tube is coupled with the actuator;
wherein the actuator is operable to move relative to the body to thereby translate both the firing beam and the closure tube, wherein the second jaw is configured to move toward the first jaw in response to translation of the closure tube, wherein the firing beam is configured to sever tissue captured between the first and second jaws;
wherein the end effector is operable to apply bipolar RF energy to tissue captured between the first and second jaws after the closure tube is translated to drive the second jaw and prior to severing of tissue by the firing beam.

20. A method of operating an end effector, the end effector comprising a first jaw, a second jaw, a firing beam, and a lockout feature, wherein the second jaw is pivotable relative to the first jaw from an open position to a closed position, wherein the firing beam comprises a sharp distal end, wherein the firing beam is translatable between the first and second jaws, wherein the lockout feature is configured to prevent translation of the firing beam, the method comprising the steps of:
(a) advancing the firing beam from a proximal position to a first distal position to thereby pivot the second jaw relative to the first jaw to the closed position;
(b) applying bipolar RF energy to the first and second jaws of the end effector;
(c) actuating the lockout feature to allow further translation of the firing beam; and
(d) advancing the firing beam from the first distal position to a second distal position to thereby sever tissue positioned between the first and second jaws.

* * * * *